(12) United States Patent
Murad et al.

(10) Patent No.: US 11,678,981 B2
(45) Date of Patent: *Jun. 20, 2023

(54) MITRAL HEART VALVE STORAGE AND HANDLING SYSTEM

(71) Applicant: Edwards Lifesciences Corporation, Irvine, CA (US)

(72) Inventors: Michael C. Murad, Lake Mathews, CA (US); Emil Karapetian, Huntington Beach, CA (US); Wesley V. Adzich, Santa Ana, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 453 days.

This patent is subject to a terminal disclaimer.

(21) Appl. No.: 17/018,804

(22) Filed: Sep. 11, 2020

(65) Prior Publication Data

US 2020/0405483 A1  Dec. 31, 2020

Related U.S. Application Data

(63) Continuation of application No. 15/865,006, filed on Jan. 8, 2018, now Pat. No. 10,772,725, which is a
(Continued)

(51) Int. Cl.
*A61F 2/24* (2006.01)
*A61F 2/00* (2006.01)

(52) U.S. Cl.
CPC .......... *A61F 2/2427* (2013.01); *A61F 2/0095* (2013.01); *A61F 2/2409* (2013.01);
(Continued)

(58) Field of Classification Search
CPC .... A61F 2/2427; A61F 2/0095; A61F 2/2409; A61F 2/2412; A61F 2220/0075; A61F 2230/0006; A61F 2250/001
See application file for complete search history.

(56) References Cited

U.S. PATENT DOCUMENTS

| 4,101,031 A | 7/1978 | Cromie |
| 4,106,129 A | 8/1978 | Carpentier et al. |

(Continued)

FOREIGN PATENT DOCUMENTS

| WO | 9725004 A1 | 7/1997 |
| WO | 0042950 A2 | 7/2000 |
| WO | 2004026173 A2 | 4/2004 |

OTHER PUBLICATIONS

Edwards Lifesciences, "Introducing the New Carpentier Edwards Perimount Magna Aortic Valve Holder," 2005; 2 pages.
(Continued)

*Primary Examiner* — Richard G Louis
*Assistant Examiner* — Chima U Igboko
(74) *Attorney, Agent, or Firm* — Guy Cumberbatch

(57) ABSTRACT

An improved holder and storage system for a tissue-type prosthetic mitral heart valve that constricts the commissure posts of the valve and prevents suture looping. A rod axially movable relative to the holder tensions lengths of attachment sutures that extend between the commissure post tips to create a tent and flex the tips inward, thus helping to prevent looping of any of an array of pre-implanted sutures around the leading tips during delivery of the valve. The holder has a safety mechanism that prevents valve delivery before the rod is deployed. One embodiment automatically deploys the rod upon opening a storage jar. One embodiment permits a delivery handle to directly deploy the rod, while another uses a separate worm screw and coupling. A holder clip that attaches to a packaging sleeve may be formed of flexible members meshed together from which the heart valve and holder are easily pulled free to eliminate a step of decoupling the clip from the sleeve.

20 Claims, 14 Drawing Sheets

Related U.S. Application Data continuation of application No. 15/076,107, filed on Mar. 21, 2016, now Pat. No. 9,861,478, which is a continuation of application No. 14/637,230, filed on Mar. 3, 2015, now Pat. No. 9,289,293, which is a continuation of application No. 13/469,975, filed on May 11, 2012, now Pat. No. 8,968,394.

(60) Provisional application No. 61/485,480, filed on May 12, 2011.

(52) U.S. Cl.
CPC .... *A61F 2/2412* (2013.01); *A61F 2220/0075* (2013.01); *A61F 2230/0006* (2013.01); *A61F 2250/001* (2013.01)

(56) References Cited

U.S. PATENT DOCUMENTS

| | | | |
|---|---|---|---|
| 4,182,446 A | 1/1980 | Penny | |
| 4,211,325 A | 7/1980 | Wright | |
| 4,697,703 A | 10/1987 | Will | |
| 4,801,015 A | 1/1989 | Lubock et al. | |
| 4,865,600 A | 9/1989 | Carpentier et al. | |
| 5,037,434 A | 8/1991 | Lane | |
| 5,167,223 A | 12/1992 | Koros et al. | |
| 5,236,450 A | 8/1993 | Scott | |
| 5,403,305 A | 4/1995 | Sauter et al. | |
| 5,476,510 A | 12/1995 | Eberhardt et al. | |
| 5,480,425 A | 1/1996 | Ogilive | |
| 5,531,785 A | 7/1996 | Love et al. | |
| 5,560,487 A | 10/1996 | Starr | |
| 5,578,076 A | 11/1996 | Krueger et al. | |
| 5,582,607 A | 12/1996 | Lackman | |
| 5,615,770 A | 4/1997 | Applebaum et al. | |
| 5,690,226 A | 11/1997 | N'Guyen | |
| 5,716,401 A | 2/1998 | Eberhardt et al. | |
| 5,720,391 A | 2/1998 | Dohm et al. | |
| 5,776,187 A | 7/1998 | Krueger et al. | |
| 5,800,531 A | 9/1998 | Cosgrove et al. | |
| 5,823,342 A | 10/1998 | Caudillo et al. | |
| 5,868,253 A | 2/1999 | Krueger et al. | |
| 5,980,569 A | 11/1999 | Scirica | |
| 5,984,959 A | 11/1999 | Robertson et al. | |
| 6,090,138 A | 7/2000 | Chasak et al. | |
| 6,126,007 A | 10/2000 | Kari et al. | |
| 6,197,053 B1 | 3/2001 | Cosgrove et al. | |
| 6,199,696 B1 | 3/2001 | Lytle et al. | |
| 6,214,043 B1 * | 4/2001 | Krueger | A61F 2/2427 623/2.11 |
| 6,231,601 B1 | 5/2001 | Myers et al. | |
| 6,346,094 B2 | 2/2002 | West et al. | |
| 6,409,758 B2 | 6/2002 | Stobie et al. | |
| 6,416,547 B1 | 7/2002 | Erickson et al. | |
| 6,534,004 B2 | 3/2003 | Chen et al. | |
| 6,591,998 B2 | 7/2003 | Haynes et al. | |
| 6,702,852 B2 | 3/2004 | Stobie et al. | |
| 6,723,122 B2 | 4/2004 | Yang et al. | |
| 6,736,845 B2 | 5/2004 | Marquez et al. | |
| 6,964,682 B2 | 11/2005 | Nguyen-Thien-Nhon et al. | |
| 6,966,925 B2 | 11/2005 | Stobie | |
| 7,018,407 B1 | 3/2006 | Wright | |
| 7,033,390 B2 | 4/2006 | Johnson et al. | |
| 7,189,258 B2 | 3/2007 | Johnson et al. | |
| 7,389,874 B2 | 6/2008 | Quest et al. | |
| 7,468,073 B2 | 12/2008 | Johnson et al. | |
| 7,503,929 B2 | 3/2009 | Johnson et al. | |
| 7,658,763 B2 | 2/2010 | Stobie | |
| 7,699,168 B2 | 4/2010 | Ryan et al. | |
| 7,712,606 B2 | 5/2010 | Salahieh et al. | |
| 7,819,915 B2 | 10/2010 | Stobie et al. | |
| RE42,395 E | 5/2011 | Wright et al. | |
| 2002/0120328 A1 | 8/2002 | Pathak et al. | |
| 2004/0024451 A1 | 2/2004 | Johnson et al. | |
| 2004/0059413 A1 | 3/2004 | Argento | |
| 2004/0148017 A1 * | 7/2004 | Stobie | A61F 2/2427 623/2.11 |
| 2005/0251252 A1 | 11/2005 | Stobie | |
| 2006/0195183 A1 | 8/2006 | Navia et al. | |
| 2007/0156234 A1 | 7/2007 | Adzich et al. | |
| 2009/0130162 A2 | 5/2009 | Pathak et al. | |
| 2009/0164005 A1 | 6/2009 | Dove et al. | |
| 2009/0259305 A1 | 10/2009 | Lane et al. | |
| 2011/0147251 A1 | 6/2011 | Hodshon et al. | |

OTHER PUBLICATIONS

Medtronic, "The Cinch Advanced Implant System Technology Made Easy," 2003; 2 pages.
Sorin Group Canada Inc. Mitroflow Division, "Aortic Pericardial Heart Valve Instructions for Use," 2004; 2 pages.
St. Jude Medical, "Experience Ease of Implant with Just One Touch," 2005; 4 pages.
St. Jude Medical, "Physician's Manual SJM Biocor Valve," Aug. 6, 2006; 5 pages.
International Search Report from corresponding International Application No. PCT/ US2011/062637 dated Nov. 30, 2011.
Medtronic, "Advanced implant System" 2003; 2 pages.
Edwards Lifesciences, "Holder Valve Peri," Sep. 15, 2005; 1 Drawing Page.
International Search Report from corresponding International Application No. PCT/ US2011/024904 dated Oct. 25, 2011.

\* cited by examiner

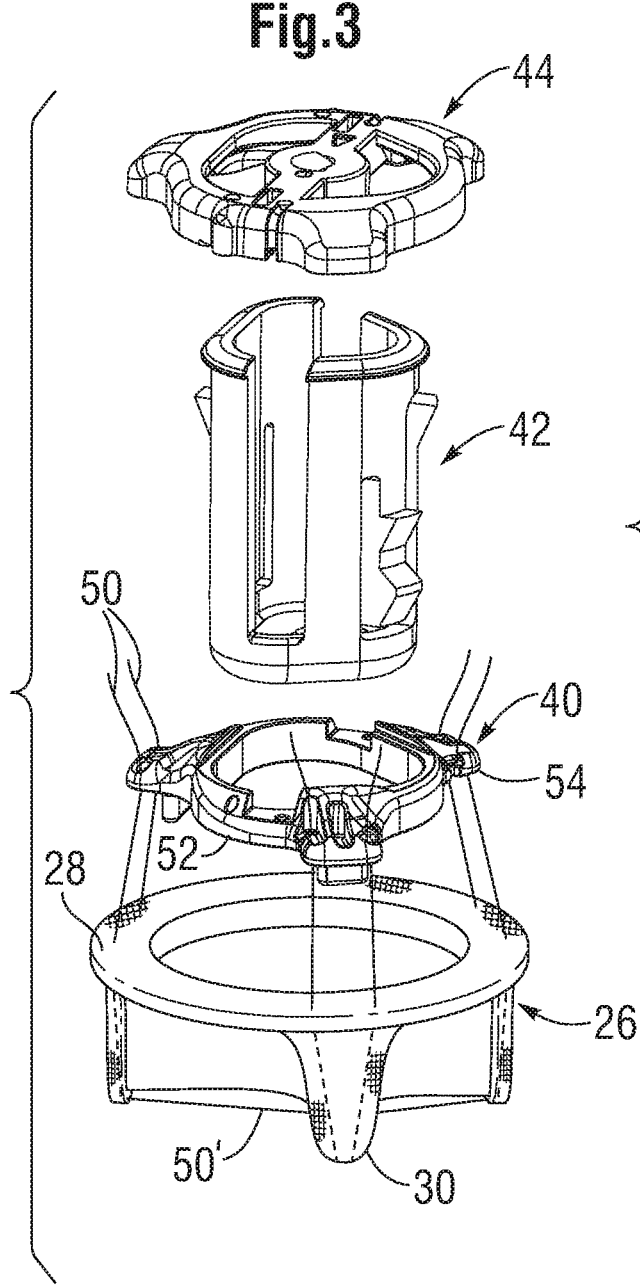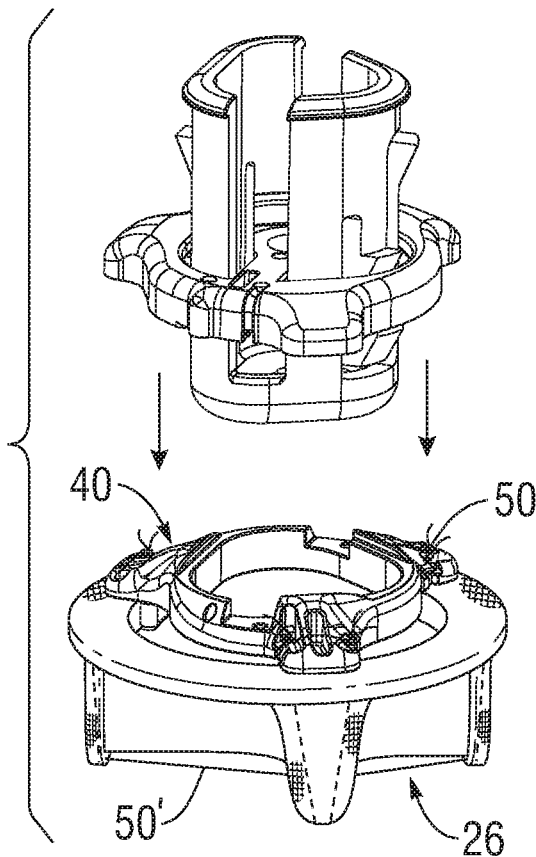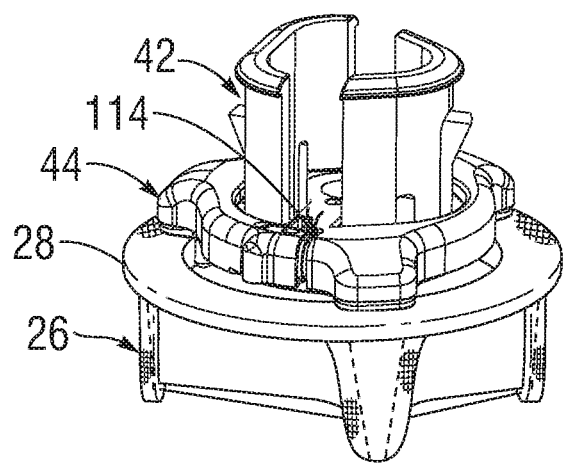

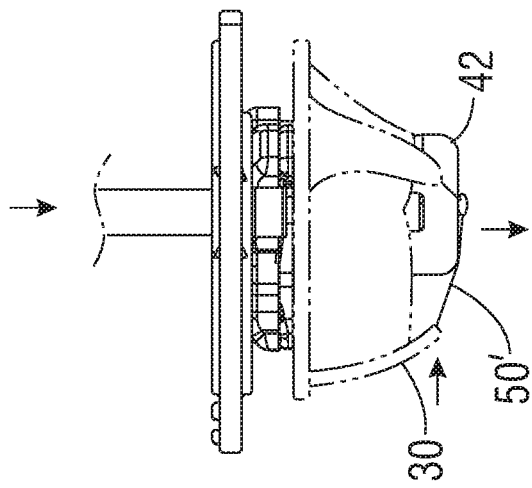
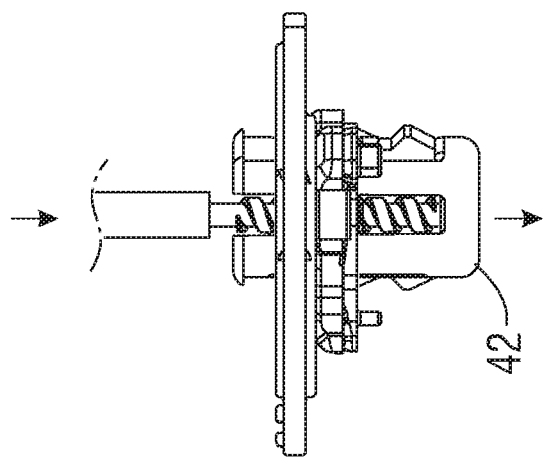
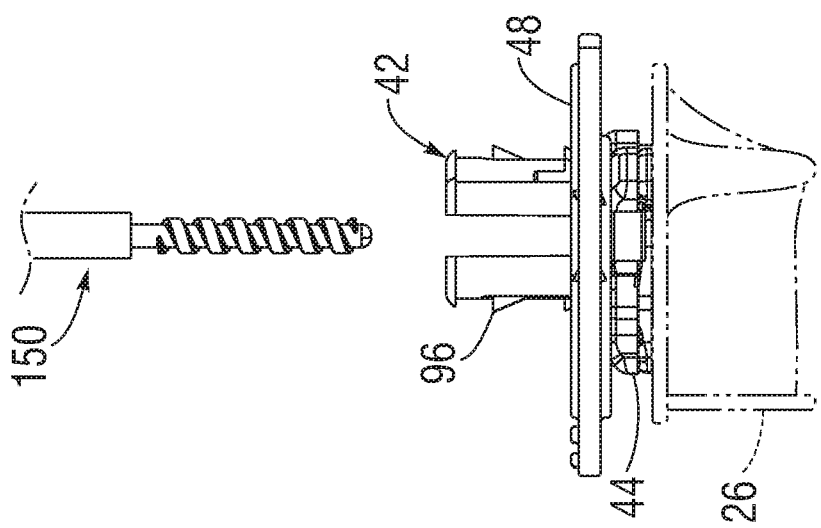

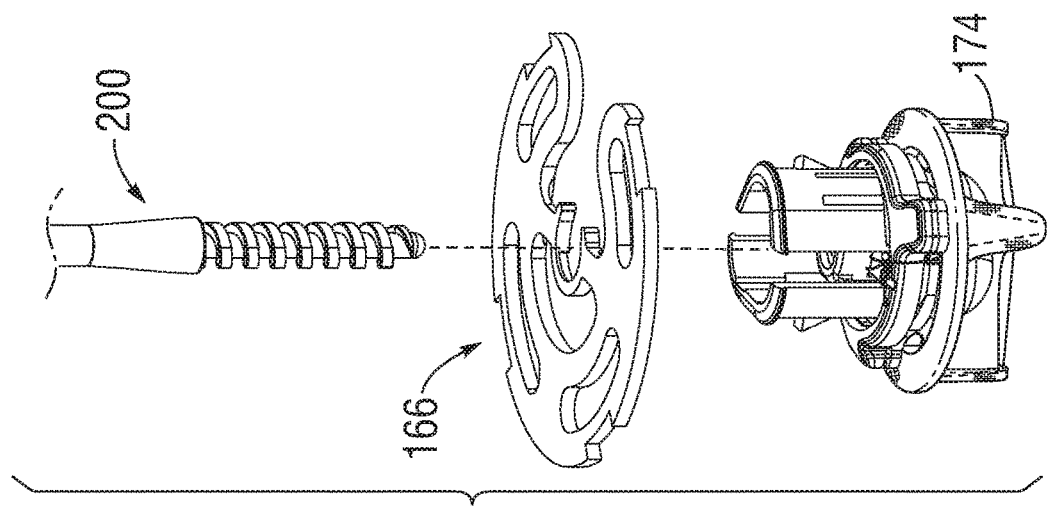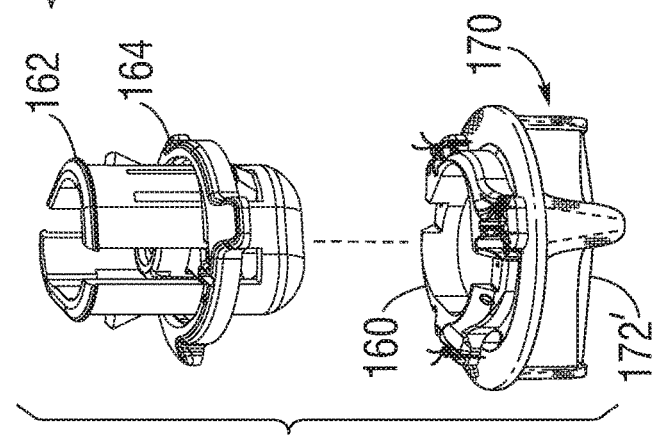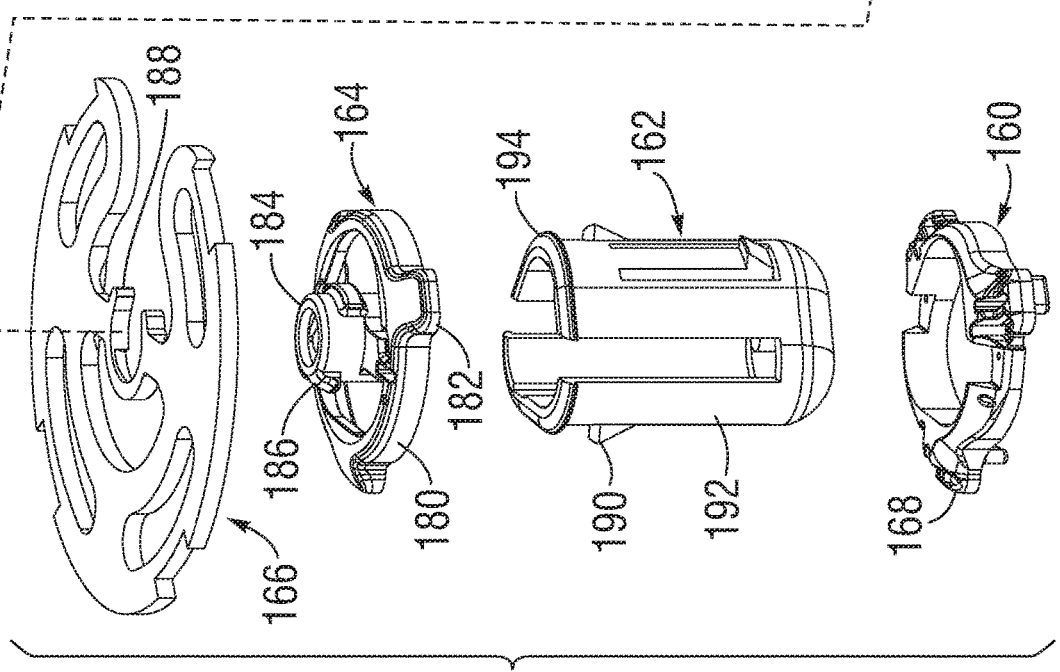

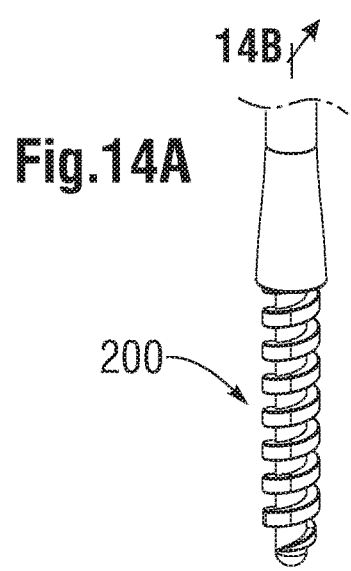
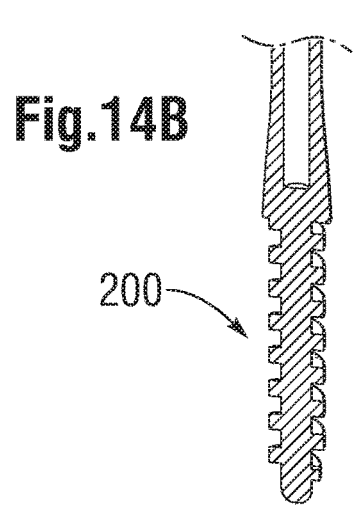
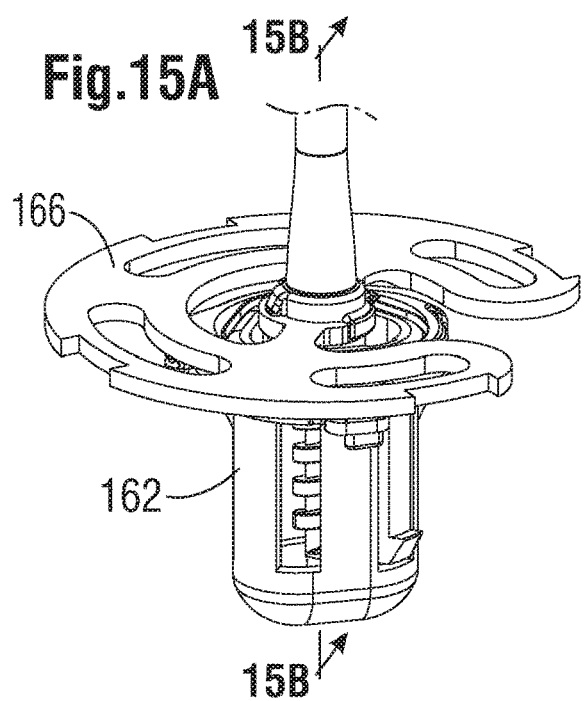
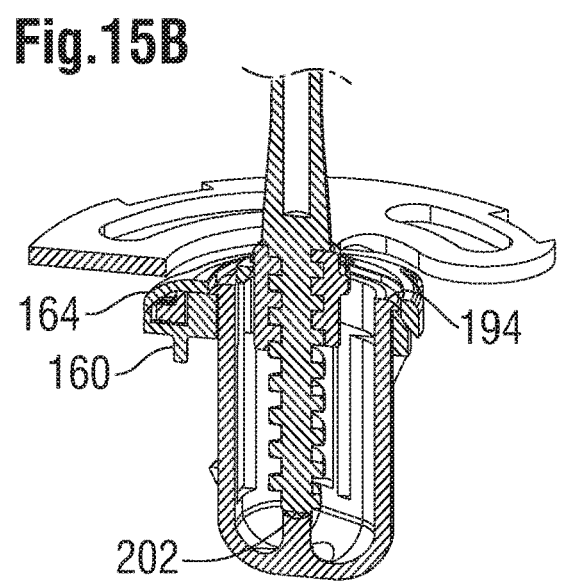

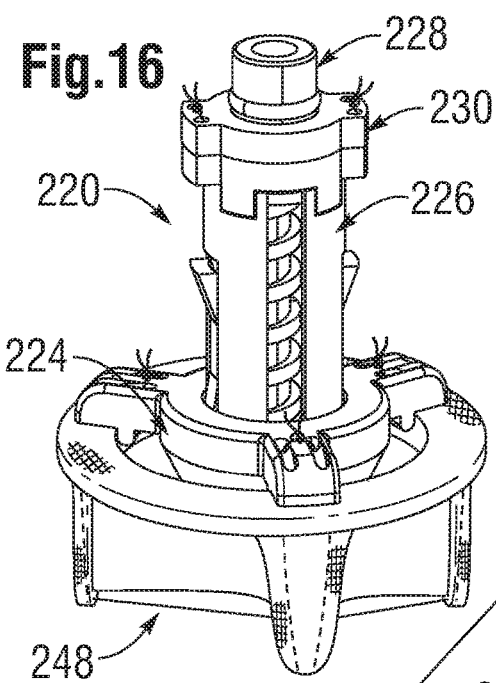
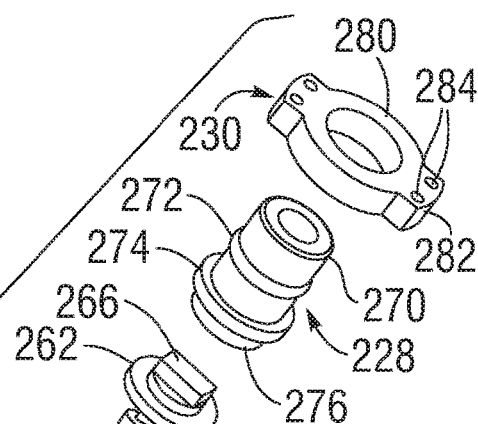
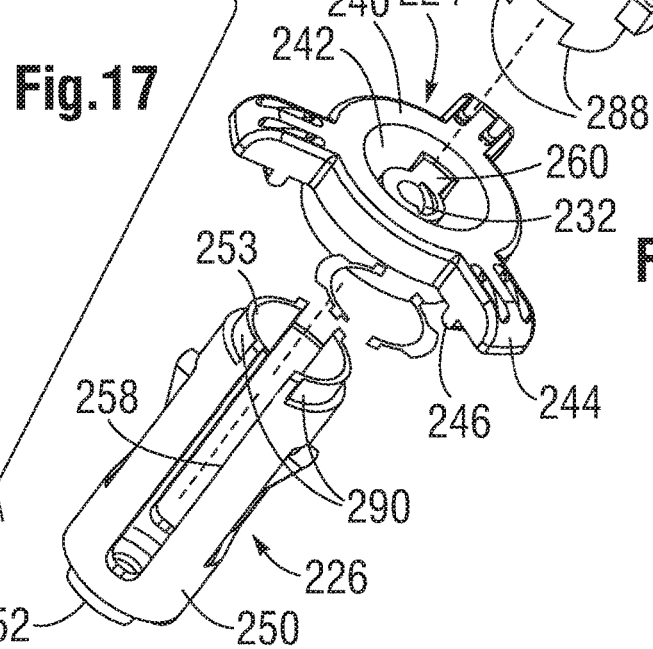
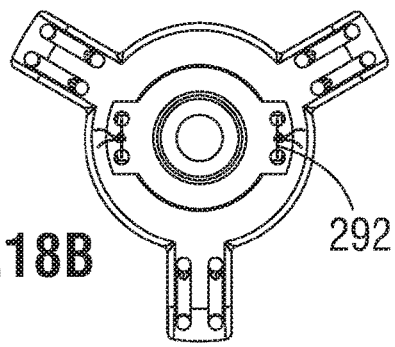
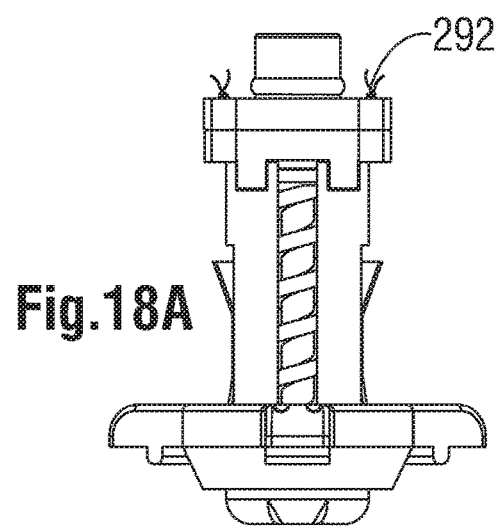

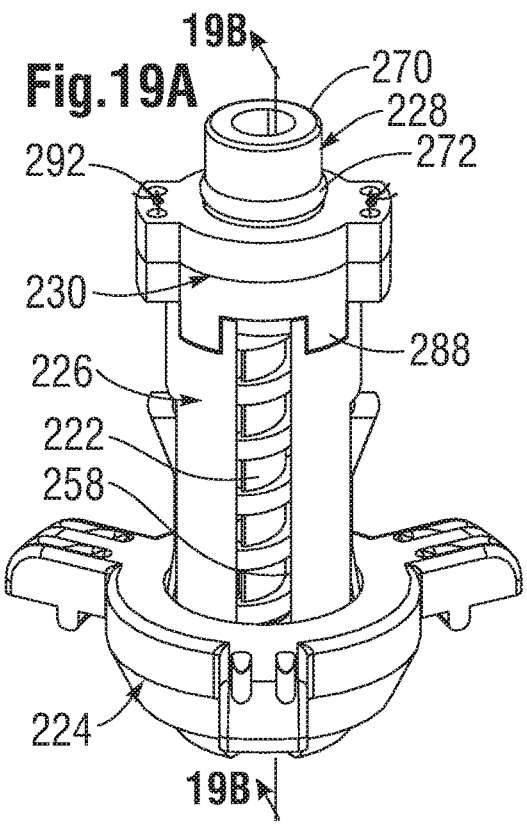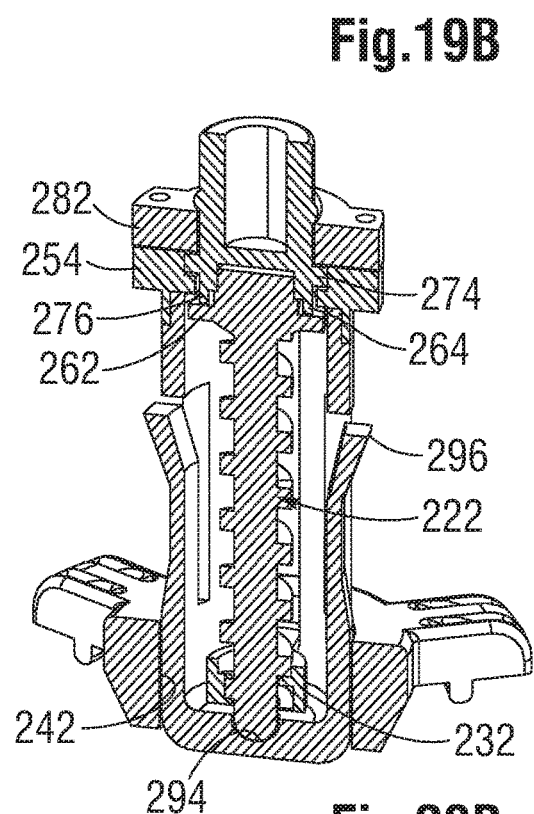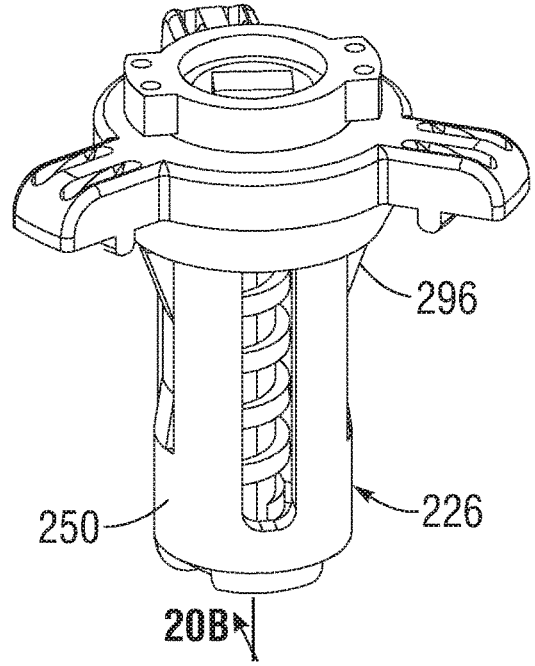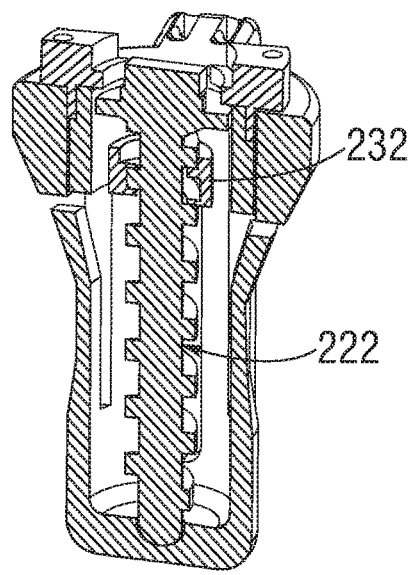

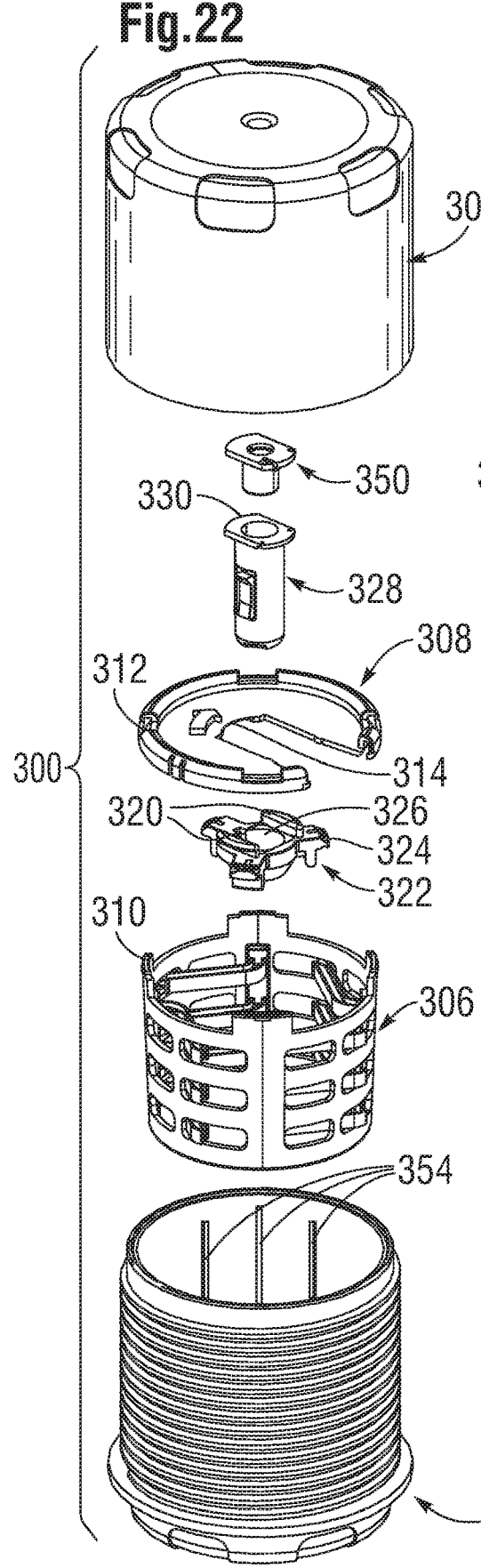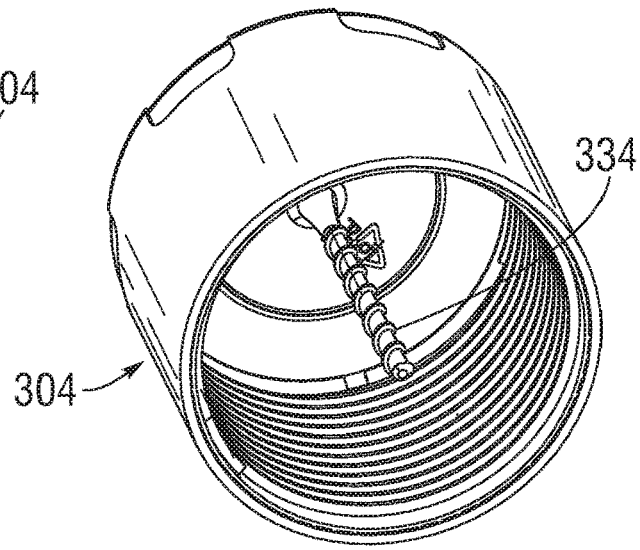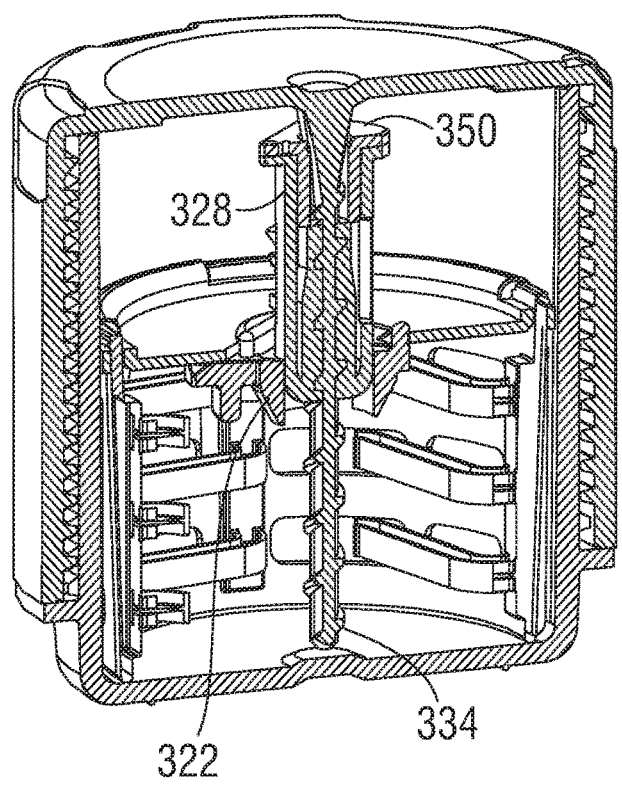

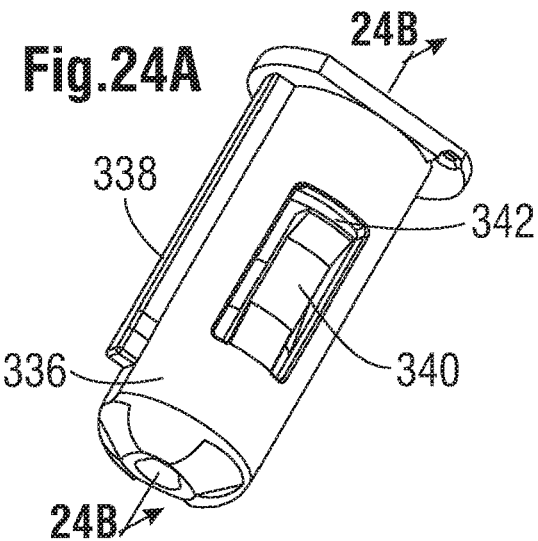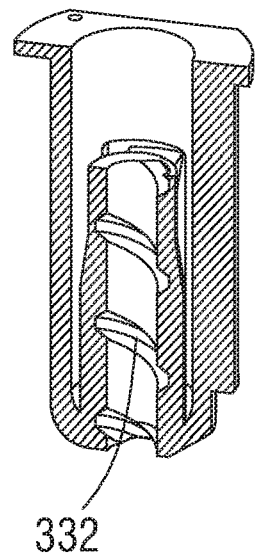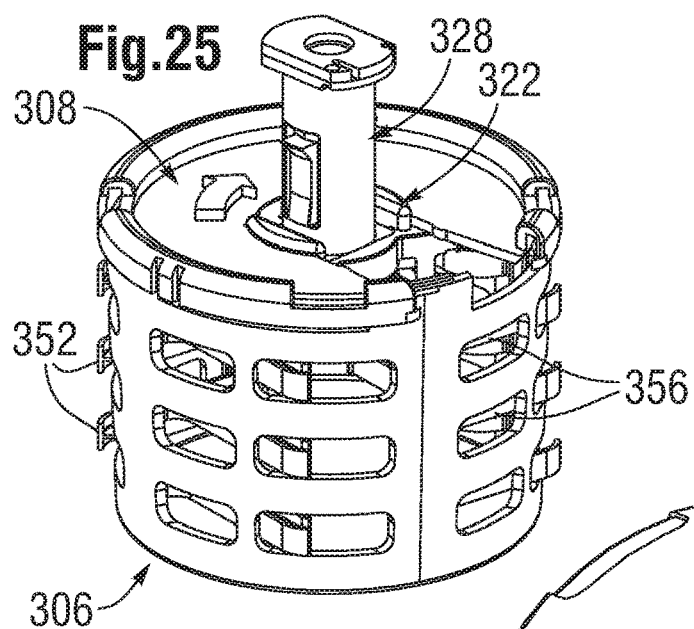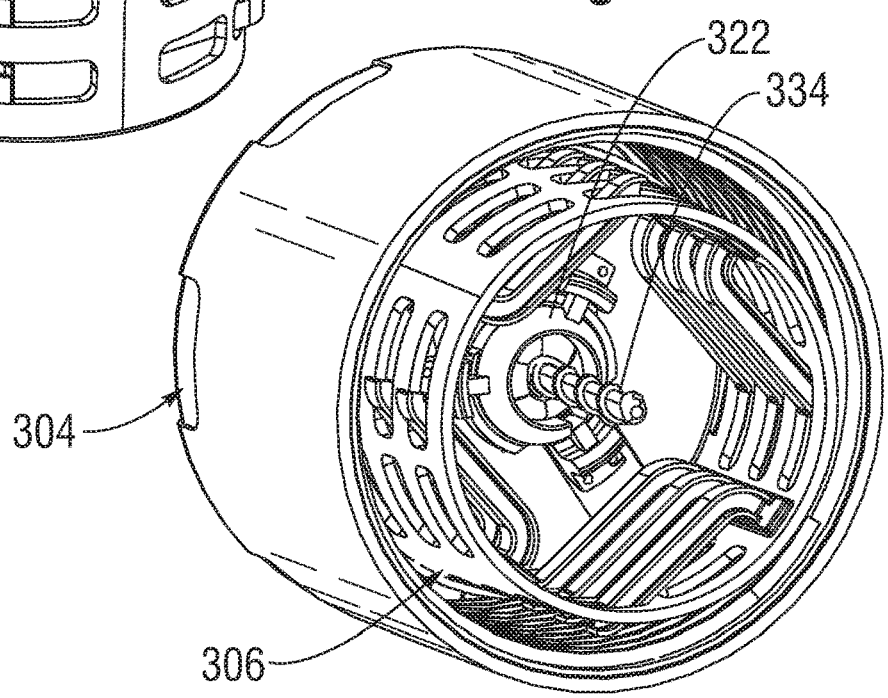

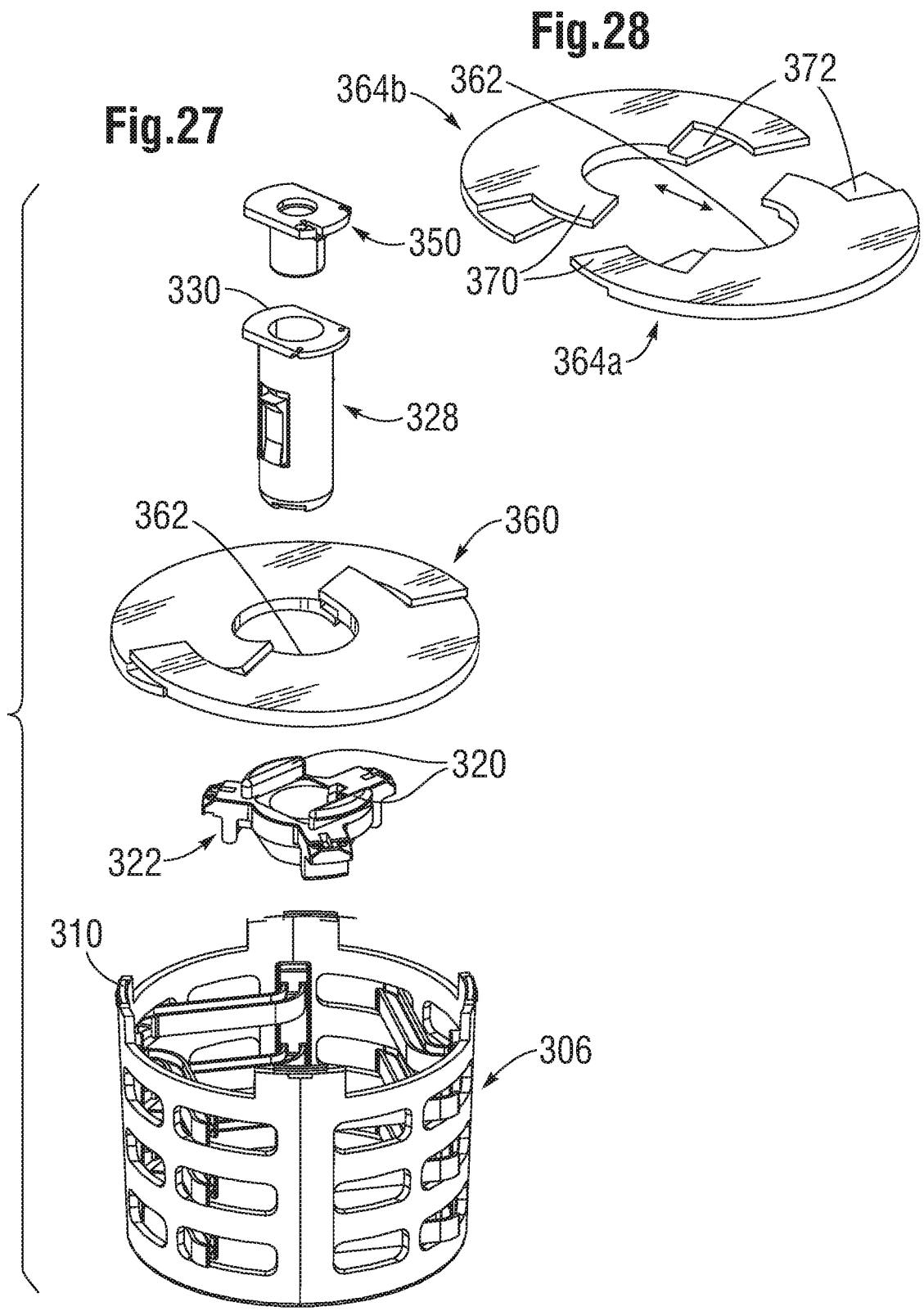

MITRAL HEART VALVE STORAGE AND HANDLING SYSTEM

CROSS REFERENCE TO RELATED APPLICATIONS

This application is a continuation of U.S. patent application Ser. No. 15/865,006, filed Jan. 8, 2018, now U.S. Pat. No. 10,772,725, which is a continuation of U.S. patent application Ser. No. 15/076,107, filed Mar. 21, 2016, now U.S. Pat. No. 9,861,478, which is a continuation of U.S. patent application Ser. No. 14/637,230, filed Mar. 3, 2015, now U.S. Pat. No. 9,289,293, which is a continuation of U.S. patent application Ser. No. 13/469,975, filed May 11, 2012, now U.S. Pat. No. 8,968,394, which claims the benefit of U.S. Patent Application No. 61/485,480, filed May 12, 2011, the entire disclosures all of which are incorporated by reference for all purposes.

FIELD OF THE INVENTION

The present invention relates generally to medical devices, and more particularly to a holder that facilitates the implantation of a bioprosthetic mitral heart valve, and also to packaging for mitral valves that facilitates commissure constriction.

BACKGROUND OF THE INVENTION

Heart valve disease is a significant cause of morbidity and mortality, resulting from a number of ailments including rheumatic fever and birth defects. The natural heart valves are identified as the aortic, mitral (or bicuspid), tricuspid and pulmonary valves, and each has leaflets to control the directional flow of blood through the heart. Worldwide, approximately 300,000 heart valve replacement surgeries are performed annually, and about one-half of these patients receive bioprosthetic heart valve replacements, which utilize biologically derived tissues for flexible fluid-occluding leaflets.

The most successful bioprosthetic materials for flexible leaflets are whole porcine valves and separate leaflets made from bovine pericardium stitched together to form a tri-leaflet valve. However, flexible leaflets formed of polymeric, fiber-reinforced, and other synthetic materials have also been proposed. The most common flexible leaflet valve construction includes three leaflets mounted to commissure posts around a peripheral support structure with free edges that project toward an outflow direction and meet or coapt in the middle of the flowstream. A suture-permeable sewing ring around the inflow end provides a platform for anchoring sutures.

Manufacturers stabilize bioprosthetic heart valves with bracketing structure within jars filled with preserving solution for shipping and storage prior to use in the operating theater. The valves are stabilized with various structures, including a 2- or 3-piece clip and tubular sleeve structure, such as shown in U.S. Pat. No. 6,416,547 to Erickson, et al.

Prosthetic valves typically have a delivery holder centrally located and sutured thereto, and an elongated delivery handle couples to the holder for manipulating the valve assembly during implant. Because of the standard delivery direction, the holder is attached to the inflow side such as the sewing ring for mitral valves and to the outflow side such as the stent cusps or outflow commissure tips for aortic valves.

When delivering a tissue type prosthetic valve in the mitral position, the outflow commissure posts are on the leading or blind side of the valve and may become entangled with pre-installed anchoring sutures. The difficulty of delivery is compounded if the surgery is through a minimally-invasive access channel, a technique that is becoming more common. The problem of entanglement is termed "suture looping," and means that the suture that is used to attach or mount the valve to the heart tissue is inadvertently wrapped around the inside of one or more of the leading commissure post tips. If this occurs, the looped suture may damage one of the tissue leaflets when tightly tied down, or may interfere with the valve implant procedure and prevent maximum coaptation of the valve leaflets, resulting in a deficiency in the prosthetic mitral valve, requiring an immediate explant.

Some attempts have been made to overcome these problems in current holders for prosthetic mitral valves. An example of such a holder is U.S. Pat. No. 4,865,600, Carpentier, et al., incorporated herein by reference, which provides a holder having a mechanism that tensions attachment sutures to constrict the valve commissure posts inwardly prior to implantation. Another similar device is seen in U.S. Pat. No. 6,966,925 to Stobie, also incorporated herein by reference, which includes a shaft member positioned on the holder that is axially movable just prior to valve deployment to cause lengths of the attachment sutures to extend axially beyond the commissure posts in the fashion of a tent.

Despite a number of advances, there is still a need in the art for a holder and associated packaging for tissue-type prosthetic mitral valves that helps prevent suture looping and is more intuitive in use.

SUMMARY OF THE INVENTION

The present application discloses storage assemblies and systems for a flexible leaflet prosthetic heart valve that helps prevent suture looping. Each assembly includes a heart valve having an inflow end and an outflow end and a flow axis therebetween. The valve includes a plurality of generally axially-extending flexible commissure posts that end in tips circumferentially-spaced around the outflow end that support occluding flexible leaflets of the valve.

One exemplary assembly features a valve holder that contacts the inflow end of the valve and defines a central aperture. A plurality of attachment sutures each has a first end that ties to the valve holder, a middle section that extends from the first end in an outflow direction to one of the commissure post tips, extends to another one of the commissure post tips, and then extends in an inflow direction back to the valve holder, and a second end tied to the valve holder. The middle section crosses the flow axis of the valve between the commissure post tips. An adapter shaped to conform to an inflow side of the valve holder attaches thereto, the adapter defines a central aperture generally aligned with the valve holder central aperture and has a bridge across the aperture with a threaded nut centered thereon. A commissure constriction rod is arranged to slide longitudinally through the valve holder aperture and adapter aperture. The rod has a closed bottom end toward the outflow direction and an open top end toward the inflow direction surrounded by a rim larger than the aperture of the valve holder but smaller than the aperture of the adapter. A male threaded member may be screwed through the threaded nut of the adapter until it contacts the closed bottom end of the rod and forces the rod in an outflow direction from an undeployed position into contact with the middle sections of the attachment sutures that cross the flow axis. The rod is then movable farther in the outflow direction to a deployed position which places the attachment sutures in tension and accordingly pulls the commissure post tips inward.

Both the adapter and valve holder desirably have through holes for receiving attachment sutures that couple the adapter and valve holder together. In one embodiment, the adapter covers locations on the valve holder where the attachment sutures to the prosthetic valve cross over cutting guides on the holder, so as to impede detachment of the holder from the valve prior to detachment of the adapter from the holder. The assembly may further include a disc-shaped clip that removably couples to the adapter and extends outward from the prosthetic heart valve, a packaging sleeve connected to the clip that substantially surrounds the prosthetic heart valve without touching it, and a storage jar sized to closely receive the packaging sleeve, wherein the packaging sleeve and storage jar include anti-rotation features that limit their relative axial rotation. The clip defines a central aperture through which the commissure constriction rod slides, wherein the commissure constriction rod may include vertical slots that permit passage of the adapter bridge, and the clip includes inwardly-directed lugs that extend within the vertical slots. In this way, the clip can only be removed laterally from the adapter after the commissure constriction rod has reached the deployed position. The clip may comprise two flexible halves that mesh together along a mid-line in a manner that resists downward movement of the valve holder but permits the valve holder and heart valve to be axially pulled upward free of the holder clip. The commissure constriction rod preferably includes opposed lockout pawls on cantilevered fingers that flex inward during passage through the valve holder aperture and spring outward underneath the valve holder to maintain the commissure constriction rod in the deployed position. Indeed, the commissure constriction rod preferably has a second set of opposed lockout pawls on cantilevered fingers that flex inward during passage through the valve holder aperture and spring outward underneath the valve holder during movement from the undeployed to the deployed position.

In accordance with another embodiment, a storage system for the flexible leaflet prosthetic heart valve comprises a storage jar having a bottom portion and a lid, a packaging sleeve that fits closely within the storage jar and defines a hollow inner space, a disc-shaped clip connected to the packaging sleeve, and the prosthetic heart valve. The system includes a valve holder that contacts the inflow end of the valve and has a central aperture, the valve holder being removably secured to the disc-shaped clip such that the heart valve is suspended within the hollow inner space of the packaging sleeve. A bridge is held stationary with respect to the valve holder and has a threaded nut thereon. A plurality of attachment sutures each has first and second ends tied to the valve holder and a middle section that extends along two of the valve commissure posts and crosses the flow axis of the valve between the commissure post tips. A commissure constriction rod is arranged to slide longitudinally through the valve holder aperture, the rod having a closed bottom end toward the outflow direction and an open top end toward the inflow direction. A male threaded member may be screwed through the threaded nut of the bridge until it contacts the closed bottom end of the rod and forces the rod in an outflow direction from an undeployed position until it contacts the middle sections of the attachment sutures on the flow axis connecting the valve holder to the prosthetic heart valve. The rod is then movable farther in the outflow direction to a deployed position which places the attachment sutures in tension and accordingly pulls the commissure post tips inward.

In the aforementioned system, the bridge and threaded nut may be integrally formed with the valve holder. The system may further have an adapter shaped to conform to an inflow side of the valve holder and attached thereto, the adapter defining a central aperture and having the bridge across the aperture with the threaded nut centered thereon. Desirably, the adapter covers locations on the valve holder where the attachment sutures to the prosthetic valve cross over cutting guides on the holder, so as to impede detachment of the holder from the valve prior to removal of the adapter from the holder. The system may also include a worm screw having threads that conform to those of the threaded nut, and a screw couple having engagement structure for contacting and rotating a proximal end of the worm screw and being removably attachable to a proximal end of the commissure constriction rod. In use, the screw couple may be rotated to cause the worm screw to advance along the threaded nut and displace the commissure constriction rod to its deployed position, and the screw couple may be detached from the commissure constriction rod and removed, leaving the worm screw engaged with the threaded nut. Moreover, an adapter sleeve that receives and retains a portion of the screw couple and permits free rotation thereof may be provided, the adapter sleeve having a flange for removably attaching to a proximal end of the commissure constriction rod, wherein the screw couple may be rotated from a proximal side of the adapter sleeve. Preferably, the adapter sleeve attaches to the proximal end of the commissure constriction rod with sutures, and the adapter sleeve and screw couple can be removed from engagement with the commissure constriction rod by severing the sutures. The screw couple may include internal threading at a proximal end for mating with a male threaded member.

In a particularly expeditious embodiment, a storage system for the flexible leaflet prosthetic heart valve comprises a storage jar having a bottom portion and a lid attached thereon, the prosthetic heart valve, a valve holder including a mechanism for pulling the commissure post tips inward, and structure within the storage jar that actuates the mechanism for pulling the commissure post tips inward upon detaching the lid from the bottom portion. The structure within the storage jar may include a male threaded member projecting downward from the jar lid, and the mechanism for pulling the commissure post tips inward includes a female threaded portion that the male threaded member engages.

In the previous system, the valve holder preferably contacts the inflow end of the valve and has a central aperture, and the mechanism for pulling the commissure post tips inward includes a plurality of attachment sutures each having first and second ends tied to the valve holder and a middle section that extends along two of the valve commissure posts and crosses the flow axis of the valve between the commissure post tips. A commissure constriction rod is arranged to slide longitudinally through the valve holder aperture, the rod having the female threaded portion therein. The male threaded member forces the rod in an outflow direction from an undeployed position until it contacts the middle sections of the attachment sutures on the flow axis connecting the valve holder to the prosthetic heart valve, the rod is then being movable farther in the outflow direction to a deployed position which places the attachment sutures in tension and accordingly pulls the commissure post tips inward.

The commissure constriction rod desirably includes opposed lockout pawls on cantilevered fingers that flex inward during passage through the valve holder aperture and spring outward underneath the valve holder to maintain the commissure constriction rod in the deployed position. The system may further have a packaging sleeve that fits closely within the storage jar bottom portion and a holder clip attached to the top of packaging sleeve. The holder clip has a central aperture that retains the valve holder suspended over a cavity within the packaging sleeve such that the prosthetic heart valve resides within the cavity of the packaging sleeve, and comprises two flexible halves that mesh together along a mid-line in a manner that resists downward movement of the valve holder but permits the valve holder and heart valve to be axially pulled upward free of the holder clip.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIG. 3 is a perspective view of a prosthetic heart valve and holder exploded below an adapter and commissure constriction rod from the prosthetic heart valve storage system of FIG. 1;

FIGS. 4A-4C are perspective views of an assembly sequence of the prosthetic heart valve storage system components seen in FIGS. 1 and 3;

FIGS. 7A-7C show a sequence of elevational views which illustrate how the holder in the system of FIG. 1 constricts the valve commissures to help prevent suture entanglement;

FIG. 12 is an exploded perspective view of key components of a prosthetic heart valve storage system similar to that shown in FIGS. 1-11;

FIGS. 13A and 13B are perspective views of an assembly sequence of the prosthetic heart valve storage system components seen in FIG. 12;

FIGS. 14A and 14B are perspective and longitudinal sectional views of the assembled system components from FIG. 12 prior to deployment of a commissure constriction rod;

FIGS. 15A and 15B are perspective and longitudinal sectional views of the assembled system components from FIG. 12 after deployment of the commissure constriction rod;

FIG. 16 is an assembled perspective view of key components of another alternative prosthetic heart valve storage system having an integral worm screw;

FIG. 17 is an exploded perspective view of the components in FIG. 16;

FIGS. 18A and 18B are elevational and plan views of the assembly of FIG. 16;

FIGS. 19A and 19B are perspective and longitudinal sectional views of the assembled system components from FIG. 16 minus the heart valve prior to deployment of a commissure constriction rod;

FIGS. 20A and 20B are perspective and longitudinal sectional views of the assembled system components from FIG. 16 after deployment of the commissure constriction rod;

FIG. 21 is a longitudinal sectional view of an alternative prosthetic heart valve storage system having the capacity to automatically constrict the heart valve commissures upon opening a storage jar;

FIG. 22 is an exploded perspective view of the components of the system of FIG. 21;

FIG. 23 is a perspective view looking up into a jar lid of the system of FIG. 21 to illustrate a worm screw integrated into the lid;

FIGS. 24A and 24B are perspective and sectional views of a commissure constriction rod used in the system of FIG. 21;

FIG. 25 is a perspective view of a packaging sleeve assembly for holding a heart valve in the system of FIG. 21;

FIG. 26 is a view looking up into a jar lid with the assembly of FIG. 25 screwed onto a threaded post therein;

FIG. 27 is an exploded perspective view of the components of a prosthetic heart valve storage system similar to that shown in FIGS. 21-22, but with an alternative holder clip attached to the top of a packaging sleeve;

FIG. 28 is a perspective view of the alternative holder clip of FIG. 27;

DETAILED DESCRIPTION OF THE PREFERRED EMBODIMENTS

The present invention provides an improved heart valve holder for tissue-type prosthetic heart valves that facilitates implantation and reduces the chance of suture entanglement. The holder of the present invention is particularly useful for prosthetic mitral heart valves having commissure posts on the outflow side supporting flexible leaflets therebetween. The mitral position is such that the outflow end with commissure posts is the leading end as it advances toward the left ventricle during implantation, and thus the holder is attached to the inflow (i.e., trailing) end of the valve. Delivery of the valve to the mitral position involves sliding (parachuting) the valve down a plurality or array of sutures that have been pre-installed around the annulus and then passed through the valve sewing ring. The holder of the present invention constricts the valve commissure posts radially inward and at the same time moves attaching sutures axially to form a steep angle, or tent, thus helping to prevent the leading commissure posts from becoming entangled in the array of pre-installed sutures.

Figure 1:
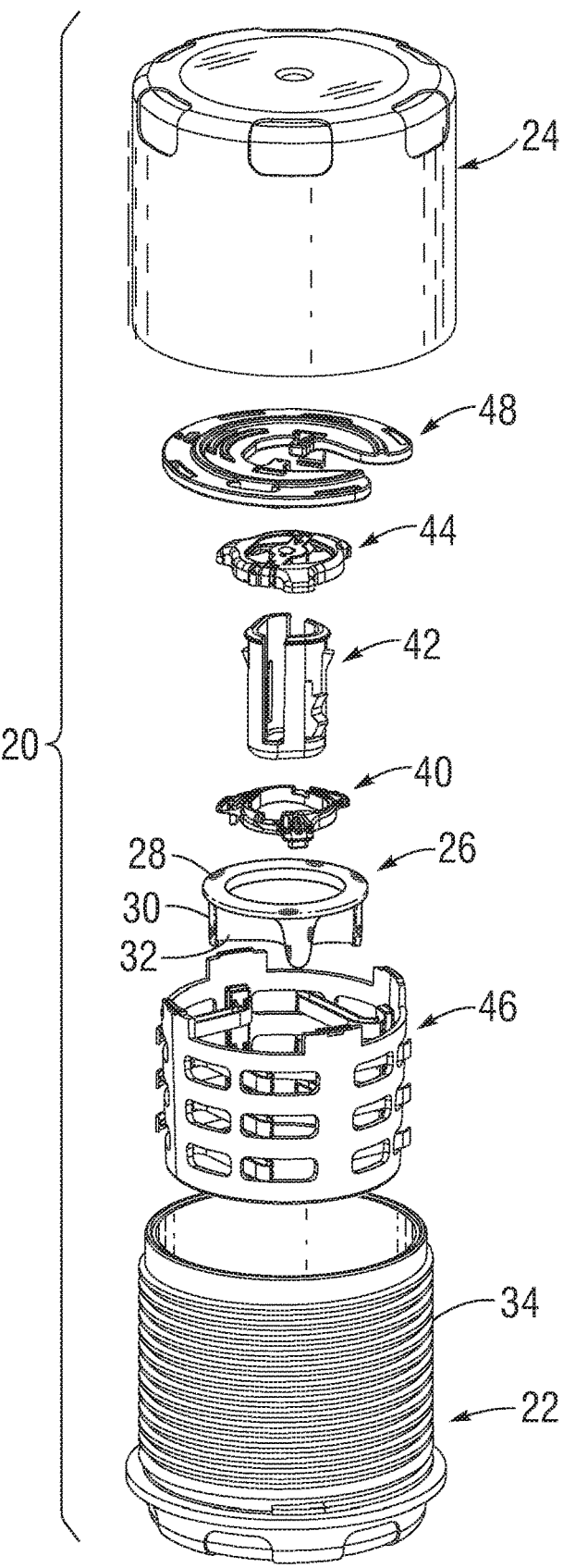
FIG. 1 is an exploded perspective view of components of an exemplary prosthetic heart valve storage system.

FIG. 1 is an exploded perspective view of components of a prosthetic heart valve storage system 20. The storage system includes a jar including a bottom portion 22 and a lid 24. A schematic flexible leaflet, typically bioprosthetic, heart valve 26 typically includes a sewing ring 28 on an inflow end, and a plurality of commissure posts 30 projecting toward an outflow end and supporting flexible leaflets 32 across a flow orifice. The remaining components seen in FIG. 1 are used to retain and stabilize the heart valve 26 within the jar, shown assembled in FIG. 2 with the lid 24 screwed onto the bottom portion 22.

The reader will notice that the bottom portion 22 includes a relatively tall series of external threads 34 that meet with internal threads (not shown) within the relatively tall lid 24. This arrangement is useful for one embodiment described below, although a more traditional jar having a shorter lid with a shorter series of mating threads is typically used. In any event, the jar contains a preservative fluid such as glutaraldehyde which maintains sterility and leaflet flexibility in bioprosthetic heart valves 26 during long-term storage, and thus the lid 24 provides a fluid tight seal over the bottom portion 22.

The components of the valve storage system 20 are shown in the various views of FIGS. 3-11, and include a valve holder 40 that attaches to the prosthetic heart valve 26, a commissure constriction rod 42, an adapter 44, a packaging sleeve 46, and a generally disc-shaped clip 48. In general, the components assemble in the sequence shown in FIG. 1 such that the heart valve 26 is restrained from movement and suspended within the fluid-filled jar for shipping and storage prior to use. The manner in which the components assemble and are used will be described below.

FIG. 3 is an exploded perspective view of the prosthetic heart valve 26 and several key components of the system 20; namely, the valve holder 40, the commissure constriction rod 42, and the adapter 44. The valve holder 40 attaches to the inflow sewing ring 28 of the valve 26 using attachment sutures 50. As seen best in FIGS. 11A-11C, the holder 40 includes a generally ring-shaped body 52 with a plurality, preferably three, outwardly-projecting legs 54. The legs 54 each include through holes 56 and a cutting guide 58 for fastening the attachment sutures 50. More particularly, free ends of attachment sutures 50 pass upward from the sewing ring 28 through two of the through holes 56 that flank the cutting guide 58. As seen in FIG. 4A, the free ends of the attachment sutures 50 are tied together so that a portion crosses over the cutting guide 58. Although not shown, each one of the free ends loops around a portion of the associated holder leg 54 so that it is secured thereto.

Figure 11A:
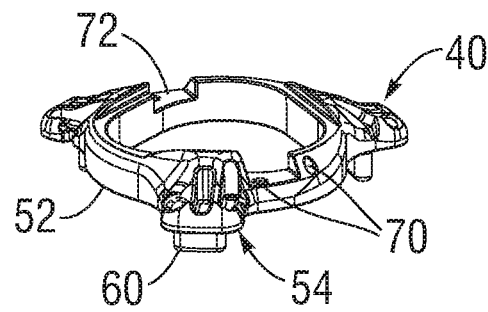
FIGS. 11A-11C are several views of a prosthetic heart valve holder used in the system of FIG. 1.
Figure 11B:
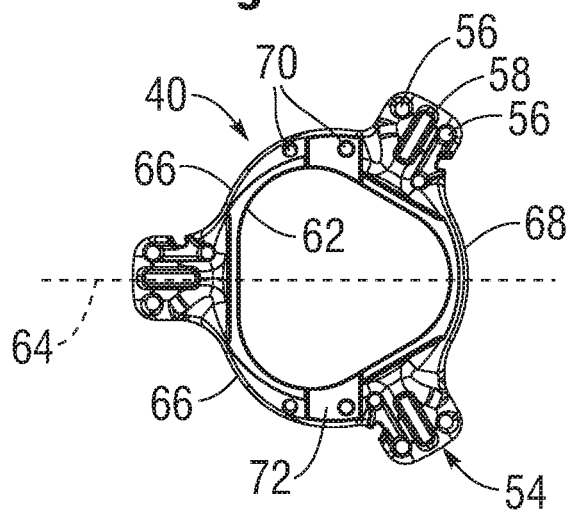

With reference again to FIG. 3, and also FIG. 11B, each of the holder legs 54 projects outwardly over one of the valve commissure posts 30. There are preferably three attachment sutures 50 that connect the holder 40 to the prosthetic heart valve 26. Each one of the attachment sutures 50 connects to one of the holder legs 54 and passes downward through the sewing ring 28 and through a fabric portion of the associated commissure posts 30. From there, the attachment suture 50 extends radially inward from a distal tip of the commissure post 30 to an axially central location (not visible) generally along the flow axis of the valve 26, and then from there radially outward to a second commissure post 30. The attachment suture 50 then extends axially upward through the second commissure post 30 and through one of the through holes 56 in a second holder leg 54, where it is also tied off. In the tri-leaflet valve 26 shown, there are three attachment sutures 50 that each have segments 50' extending between two of the commissure posts 30, with the aggregate forming a trefoil shape across the commissure tips. To ensure that the attachment sutures 50 meet at the actual center of the valve, the segments 50' overlap in the middle. The segments 50' of the attachment sutures 50 that span between the distal tips of the commissure posts 30 are arranged generally in a plane and, though tautly threaded through the valve 26 prior to use, they do not pull the commissure posts 30 inward to any great degree so that the valve can be in a relaxed state during a potentially long storage period. As will be described below, tension on the attachment sutures 50 causes inward constriction of the commissure posts 30, much as was described in U.S. Pat. No. 6,966,925 to Stobie.

Figure 10B:
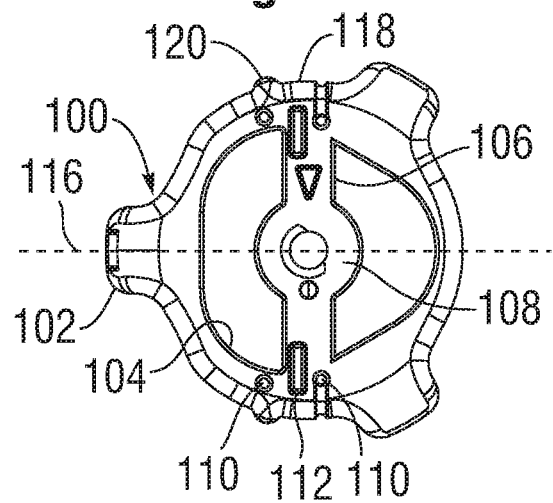
Figure 11C:
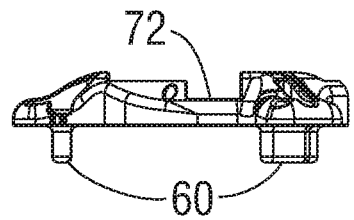

With reference still to FIG. 3 and the detailed views of FIGS. 11A-11C, the valve holder 40 includes several other features that should be noted. First of all, three downwardly-projecting flanges 60 coinciding with each of the holder legs 54 extend into the flow orifice defined by the sewing ring 28. These flanges 60 thus enable a technician to rapidly center the holder 40 on the inflow side of the valve 26 when securing it thereto with the attachment sutures 50. Furthermore, the flanges 60 provide stability between the holder 40 and attached valve 26 during the delivery and implantation procedure to help prevent radial misalignment therebetween. The holder 40 further includes a contoured or generally rounded upper face which mates with a concave underside of the adapter 44, as will be explained. With specific reference to the plan view of FIG. 11B, the ring-shaped body 52 has a rounded triangular central aperture defined by an inner boundary 62. As will be explained further, the inner boundary 62 closely receives the similarly-shaped commissure constriction rod 42. The holder 40 possesses symmetry (about a horizontal line 64 in FIG. 11B) such that two of the three spans 66 of the body 52 between the legs 54 are identical, while a third span 68 is unique. The two identical spans 66 both include through holes 70 that receive sutures for connecting the holder 40 to the adapter 44. Indeed, although the adapter 44 will be described in greater detail below, FIG. 10B adjacent to FIG. 11B shows its congruency with the holder 40. The two identical spans 66 have cutout regions 72 that are aligned across the holder 40 and serve to orient the holder relative to the adapter 44, again, as will be explained.

FIG. 4A shows the valve holder 40 secured to the heart valve 26 with the attachment sutures 50. As explained, each pair of free ends of the attachment sutures 50 ties to one of the holder legs 54. Above the valve, a subassembly of the commissure constriction rod 42 and adapter 44 is shown. To better explain these two parts, greater detail is shown in FIGS. 8A-8C and 10A-10C.

Figure 8A:
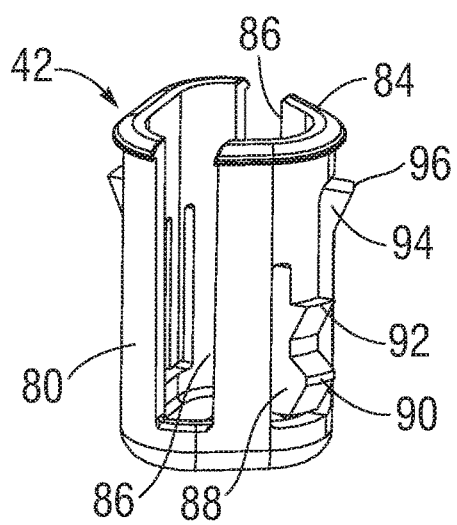
FIGS. 8A-8C are several views of a commissure constriction rod used in the system of FIG. 1.
Figure 8B:
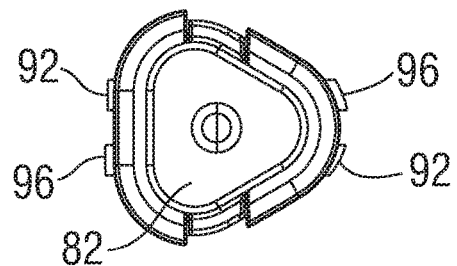
Figure 8C:
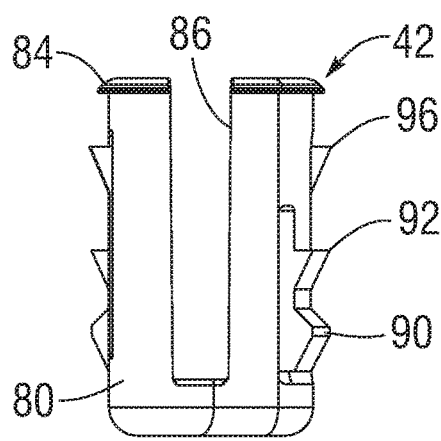

The commissure constriction rod 42 seen in FIGS. 8A-8C comprises an elongated body 80 having a closed bottom end 82 and an open top surrounded by a rim 84. As seen in FIG. 8B, a horizontal section shows that the body 80 has a rounded triangular configuration. The body 80 is formed by generally vertical sidewalls interrupted by several slots and cutouts. More particularly, two opposed vertical slots 86 substantially the entire length of the body 80, opening at the upper rim 84 and ending near to the closed bottom end 82. The vertical slots 86 engage with elements of the adapter 44 and the clip 48, as will be explained. Additionally, the body 80 includes a pair of opposed assembly fingers 88 each of which has two outwardly-projecting pawls—a two-way pawl 90 and a lockout pawl 92. Fingers 88 are formed by slits cut into the body 80 and are cantilevered downward so as to be radially flexible. The body 80 further includes a pair of opposed lockout fingers 94 that are also formed by slits cut into the body so as to be cantilevered upward and radially flexible. The lockout fingers 94 each include a single lockout pawl 96. Each of the pawls 90, 92, 96 interact with the inner boundary 62 of the valve holder 40 during assembly of the components and actuation of the rod 42. More particularly, the peripheral size and shape of the rounded triangular body 80 fits closely within the rounded triangular inner boundary 62 of the valve holder, with the pawls 90, 92, 96 projecting outwardly (see FIG. 8B) so as to provide interference with the holder inner boundary. The upper rim 84 of the rod 42 extends outwardly from the body 80 and is too large to pass through the holder inner boundary 62.

The adapter 44 fits down over the top of the rod 42, as seen by comparing FIGS. 3 and 4A. The adapter 44, illustrated in detail in FIGS. 10A-10C, includes a generally ring-shaped body 100 defining a central aperture and three outwardly-projecting legs 102. A rounded triangular inner boundary 104 is spanned by a bridge 106 across the middle of the adapter 44. An internally threaded nut 108 resides at the center of the bridge 106. The size of the inner boundary 104 is large enough to fit around the upper rim 44 of the commissure constriction rod 42 with the bridge 106 passing downward through the vertical slots 86, as seen in FIG. 4A. As mentioned previously, and as seen by a comparison of FIGS. 10B and 11B, the shape of the adapter 44 conforms to the shape of the valve holder 40, and the former ultimately lies on top of the latter and is secured thereto. More particularly, the subassembly of the rod 42 and adapter 44 is lowered down into contact with the valve holder 40 such that the adapter legs 102 register with the holder legs 54, and the lower end of the rod 42 projects within the inner boundary 62 of the holder. The adapter 44 covers locations on the valve holder 40 where the attachment sutures 50 cross over the cutting guides 58, which impedes detachment of the holder from the valve 26 prior to detachment of the adapter from the holder.

FIG. 4B illustrates the subassembly of the commissure constriction rod 42 and adapter 44 coupled with the prosthetic heart valve 26 and its holder 40. As seen in FIG. 10B, the adapter 44 includes a plurality of through holes 110 flanking a pair of cutting guides 112 located on opposite sides of the body 100. The through holes 110 align with the through holes 70 in the holder 40 (FIG. 11B) and permit passage of sutures 114 (see FIG. 4B) which are tied off such that a section spans each of the cutting guides 112. Each of these attachment sutures 114 is securely fastened to the adapter 44 such that when severed through the cutting guides 112, removal of the adapter also pulls the attachment sutures therewith.

Figure 9A:
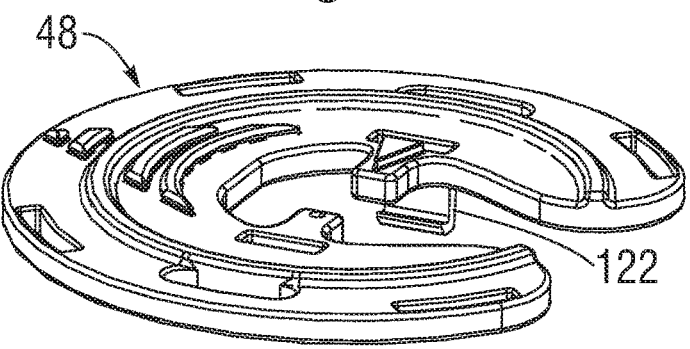
FIGS. 9A-9C are several views of a storage clip used in the system of FIG. 1.
Figure 10A:
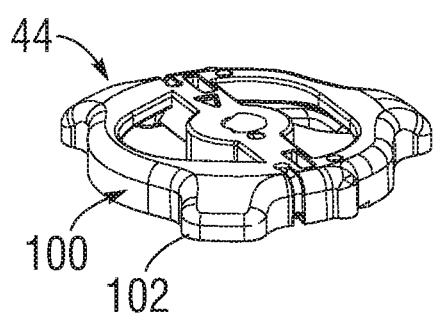
FIGS. 10A-10C are several views of an adapter having a threaded nut used in the system of FIG. 1.
Figure 10C:
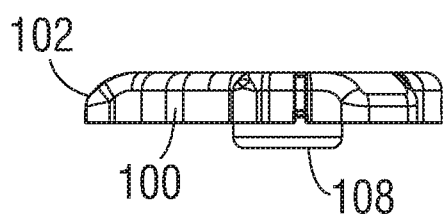

Still with reference to FIGS. 10A-10C, the adapter 44 includes a plane of symmetry 116. On opposite exterior edges of the adapter body 100 across the plane 116, short lands 118 are each defined between one of the outwardly-projecting legs 102 and a small outward bump 120. The lands 118 provide surfaces which latches 122 on the packaging clip 48 engage (FIG. 9A).

Figure 4C:
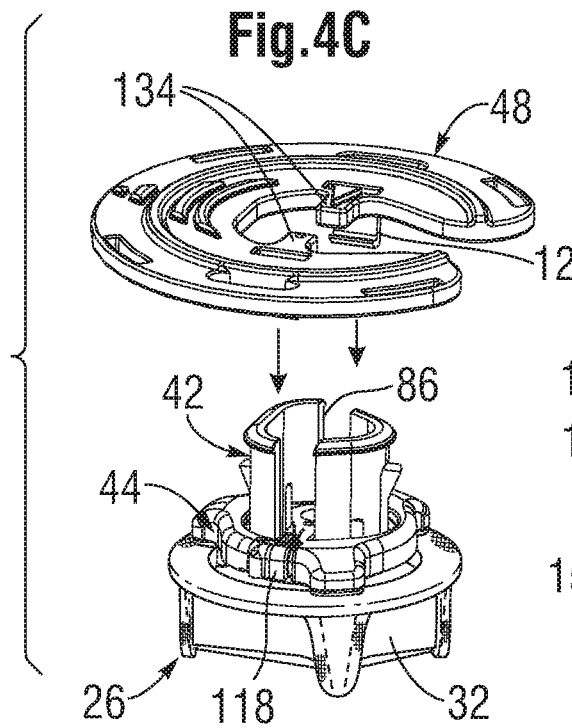
Figure 5:
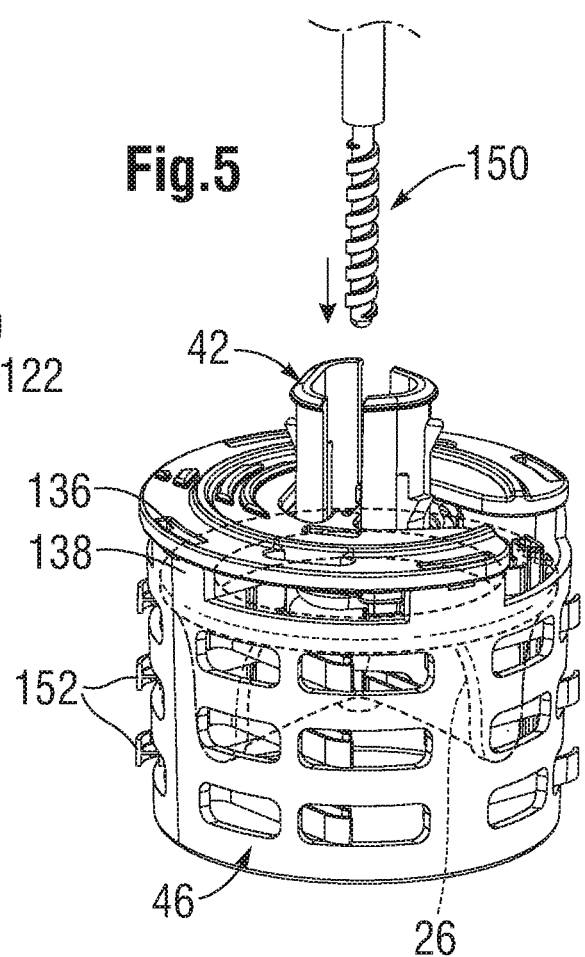
FIG. 5 is a perspective view of the assembled components from FIG. 4C placed within a storage sleeve and showing a threaded deployment handle advancing thereover.
Figure 9B:
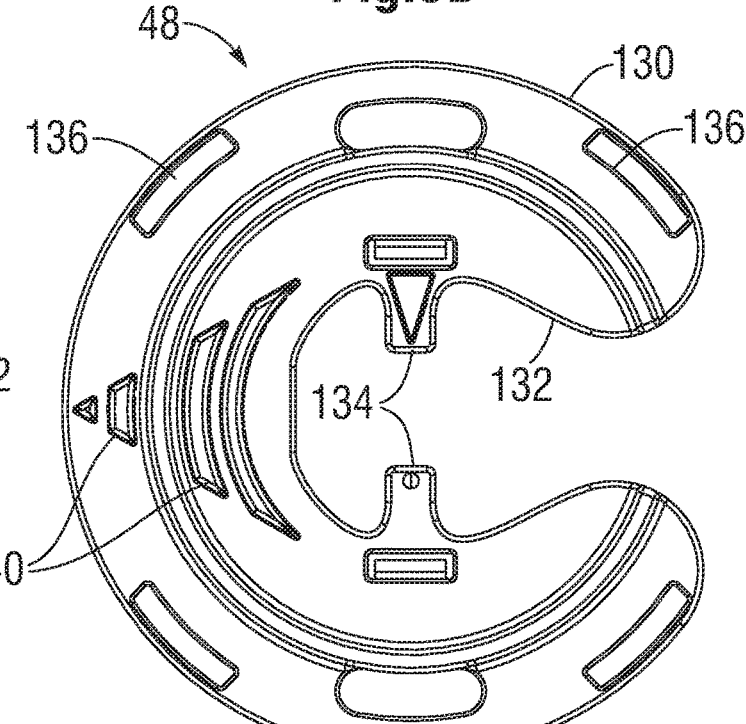
Figure 9C:

The disc-shaped packaging clip 48 shown in detail in FIGS. 9A-9C is shaped generally as the letter "C" with a circular outer periphery 130 open at one side leading to an inner boundary 132. A pair of opposed lugs 134 projecting inward from the inner boundary 132 fit within the vertical slots 86 in the rod 42, as can be seen in FIG. 4C. The clip 48 further includes a plurality of slots 136 distributed around its outer periphery for mating with upstanding fingers 138 on the packaging sleeve 46, as seen in FIG. 5. As seen in FIG. 9B, the upper surface of the disc-shaped clip 48 includes a directional indicator 140 pointing away from the opening of the "C" shape. In the illustrated embodiment, the indicator 140 comprises a series of raised ribs that gradually taper to the left in the form of an arrowhead, although a similar indicator may be formed from indentations, printing, or the like. The purpose of the indicator 140 will be explained below.

Figure 2:
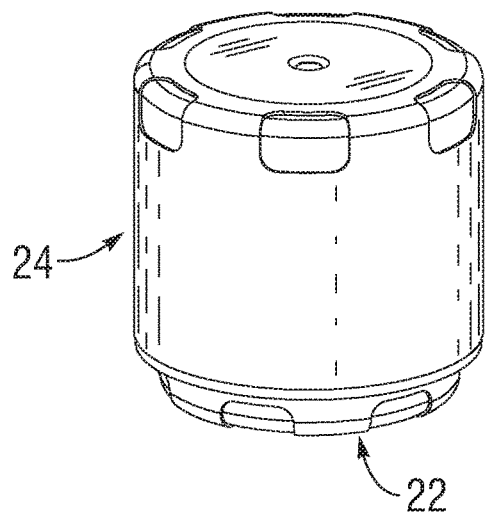
FIG. 2 is an assembled perspective view of the prosthetic heart valve storage system showing an external storage jar.

FIG. 5 illustrates the assembled components from FIG. 4C, including the clip 48 coupled down over the adapter 44, placed within the generally tubular though perforated storage sleeve 46. As mentioned above, the four upstanding fingers 138 on the sleeve 46 engage within the corresponding slots 136 in the clip 48. This structure stabilizes the prosthetic heart valve 26 that is held by the holder 42, adapter 44, and clip 48. The entire assembly shown in FIG. 5, minus an illustrated threaded deployment handle 150, is placed within the lower section 22 of the storage jar within which is provided a preserving fluid such as glutaraldehyde. The package is sealed by screwing on the lid 24, as seen in FIG. 2.

The packaging sleeve 46 has a plurality of openings or perforations around its circumference to permit relatively unimpeded flow of preservative fluid therethrough. Also, once removed from the jar, the entire assembly may easily be rinsed with a sterile solution, and the openings in the side of the sleeve 46 permit the heart valve 26 therein to be rinsed. The sleeve 46 further includes a plurality of outwardly-directed protrusions 152 that are arranged to engage inwardly-directed rails (not shown) on the interior of the jar bottom 22. Interference between the protrusions 152 and the jar rails limits rotation of the sleeve 46 within the jar to a small angular extent. This anti-rotation feature permits the threaded deployment handle 150 to be advanced and screwed into the threaded nut 108 of the adapter 44 with one hand while the other hand holds the jar, without having to otherwise brace the sleeve 46. It should be understood that various other anti-rotation configurations between the sleeve 46 and the jar are contemplated, such as shown in co-pending U.S. Pat. No. 8,839,957, entitled PROSTHETIC HEART VALVE PACKAGING SYSTEM, filed Feb. 14, 2011, whose contents are expressly incorporated by reference herein.

Figure 6A:
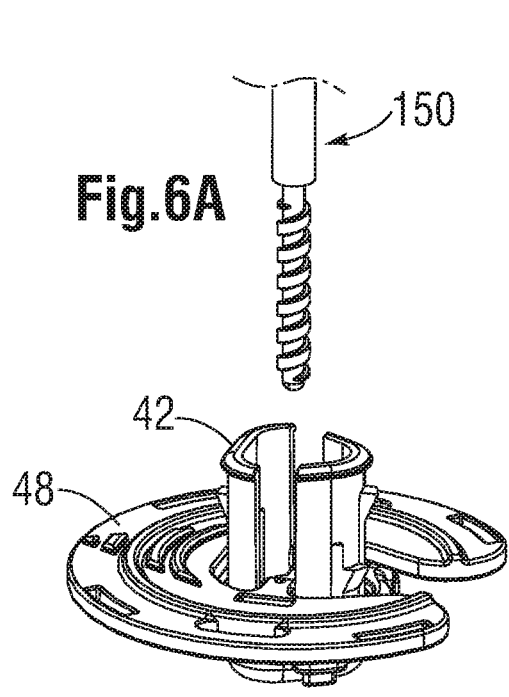
FIGS. 6A and 6B are perspective and elevational views showing select components of the storage system and delivery handle thereover.
Figure 6B:
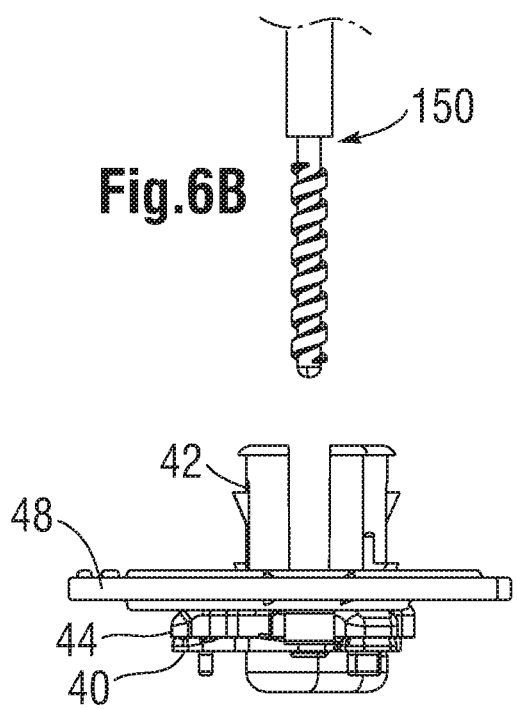

FIGS. 6A and 6B show the assembled components from FIG. 4C minus the heart valve 26 and the distal end of the threaded deployment handle 150. The elevation of the commissure constriction rod 42 relative to the valve holder 40, adapter 44, and disc-shaped clip 48 is shown. As mentioned previously, the lower end of the rod 42 projects slightly within the inflow end of the prosthetic heart valve 26, but not far enough to contact the flexible leaflets 38. The rod 42 is in its undeployed configuration. In this position, the inner boundary 62 of the valve holder 40 (see FIG. 11B) is positioned between the two-way pawl 90 and lockout pawl 92 of the assembly fingers 88 on the rod 42 (see FIG. 8B). The two-way pawl 90 permits downward passage of the rod 42 through the valve holder 40. During assembly, a technician inserts the combination of the rod 42 and adapter 44 into the holder 40, as seen in FIG. 4A, until the rod reaches this position. Further downward movement of the rod 42 will cause inward movement of the lockout pawl 92 past the inner boundary 62 of the valve holder 40, which then prevents subsequent upward movement of the rod. However, prior to this deployment, the storage system components securely suspend the prosthetic heart valve 26 within the cylindrical space defined within the sleeve 46.

FIGS. 7A-7C show a sequence of elevational views which illustrate how the valve holder 40 constricts the valve commissures 30. The threaded delivery handle 150 is advanced downward through the open end of the constriction rod 42. The male threads on the handle 150 engage the female threads on the threaded nut 108 of the adapter 44

(FIG. 10B). As the handle 150 advances, as seen in FIG. 7B, the distal end thereof contacts the closed bottom end 82 of the rod 42 and forces the rod downward. Ultimately, as seen in FIG. 7C, the lower end of the rod 42 contacts the trefoil arrangement of attachment sutures 50' and forces them downward also. Because of the finite length of the sutures 50 attached to the valve holder 40, this downward force causes them to form a tent shape which pulls the commissures 30 inward. Finally, the rod 42 advances far enough such that the upper lockout pawls 96 descend below the inner boundary 62 of the valve holder 40, thus preventing upward movement of the rod. At this point, the valve holder assembly is fully deployed and the prosthetic heart valve 26 is ready for attachment to pre-installed annulus implantation sutures and parachuted deployment down an array of such sutures.

The disc-shaped packaging clip 48 can be easily removed by pulling it off of the adapter 44. More particularly, pulling the clip in the direction of the indicator 140 of FIG. 9B causes the downward latches 122 to travel over the small bumps 120 (FIG. 10B) on the adapter 44. The orientation of the adapter 44 in FIG. 10B is the same as of the clip 48 in FIG. 9B such that is easy to see how the clip can be disengaged to the left from the adapter.

The packaging system further includes a safety mechanism whereby the clip 48 cannot be removed until the commissure constriction rod 42 has been deployed downward. More particularly, the inwardly-directed lugs 134 on the clip 48 extend within the vertical slots 86 in the rod 42. As seen best in FIGS. 6A and 7A-7C, removal of the clip 48 from the adapter 44 is prevented by the interference between the lugs 134 and slots 86 until the rod 42 has descended downward below the level of the clip 48. The upper rim 84 of the rod 42 ultimately contacts the inner boundary 62 of the holder 40 and stops downward movement of the rod. At this point, the rod 42 is below the level of the clip 48 which can be removed laterally.

In use, the packaging system 20 shown in FIGS. 1-11 facilitates deployment of the commissure constriction mechanism and thus simplifies the preparation of the prosthetic heart valves 26 prior to implantation. The components of the system 20 are coupled together as explained above and sealed within the jar as seen in FIG. 2. When ready for implantation, the surgical team removes the lid 24 from the bottom portion 22, thus exposing the top of the assembly as seen in FIG. 5 within the jar. A technician advances the delivery handle 150 downward into the open end of the commissure constriction rod 42 until it engages the threaded nut 108 on the adapter 44. The technician screws the delivery handle 150 into the threaded nut 108 until its distal end contacts the closed bottom end 82 of the rod 42, as seen in FIG. 7B. During this procedure, the preservative fluid may remain in the jar in which case the bottom portion 22 must be kept upright. Alternatively, the technician pours the preservative fluid out and can thus hold the jar in any orientation. The anti-rotation protrusions 152 on the packaging sleeve 46 (FIG. 5) engage the rails on the inner wall of the jar bottom portion 22, thus bracing the assembly from rotation while screwing in the handle 150. Another alternative is to remove the entire assembly shown in FIG. 5 from the jar and hold on to the exterior of the packaging sleeve 46 while screwing in the handle 150.

Just prior to or as the top rim 84 of the rod 42 (FIG. 8A) reaches the inner boundary 62 of the valve holder 40 (FIG. 11B), the upper lockout pawls 96 on the rod spring outward underneath the holder, which can be heard and felt by the technician. Moreover, further downward movement of the rod 42 is prevented which indicates that the valve commissures 30 are in the constricted position shown in FIG. 7C. At this point, if not already done, the technician can remove the entire assembly shown in FIG. 5 from the jar using the handle 150. The packaging sleeve 46 is easily pulled axially downward so that the upstanding fingers 138 on the sleeve disengage from the slots 136 on the disc-shaped clip 48. Because the rod 42 has descended below the level of the clip 48, the clip can be removed laterally from engagement with the adapter 44, leaving the assembly seen in FIG. 4B in addition to the delivery handle 150.

The surgeon then threads an array of pre-installed implantation sutures around the periphery of the sewing ring 28 in accordance with established practice. Subsequently, the surgeon advances the prosthetic heart valve 26 down the parachute-like array of implantation sutures until the sewing ring 28 comes in contact with the mitral valve annulus. Because the commissures 30 have been constricted radially inward, the possibility of suture entanglement is greatly reduced. Furthermore, the tented arrangement of the attachment sutures 50' and blunt distal tip of the commissure constriction rod 42, as seen in FIG. 7C, helps deflect any loose implantation sutures from looping around the commissure tips.

At this point, the sutures 114 holding the adapter 44 to the valve holder 40 can be severed, and the adapter easily removed along with the handle 150. This also exposes the cutting guides 58 on the valve holder 40, which were occluded by the adapter 44. Preventing removal of the valve holder 40 from the valve 26 until the adapter 44 is removed further ensures that the commissures have been constricted, because the adapter 44 cannot be removed until the packaging clip 48 has been removed therefrom, which can only happen after the rod 42 has fully descended.

The delivery handle 150 is useful to control movement of the heart valve 26, but after valve contact with the annulus the handle is desirably removed to improve access to the space around the valve and facilitate tying off implantation sutures on the visible side of the sewing ring 28. Because of the lockout pawls 96 on the commissure constriction rod 42, the delivery handle 150 and adapter 44 can be easily removed while the commissure constriction mechanism remains in place.

After tying down the implantation sutures, the surgeon then severs the attachment sutures 50 seen in FIG. 4A that couple the holder 40 to the prosthetic heart valve 26. Because one end of each of the sutures 50 is secured to the holder 40, severing the sutures at the cutting guides 58 (FIG. 11B) permits the holder and sutures to be pulled free of the heart valve 26, thus completing the implantation procedure.

FIG. 12 is an exploded perspective view of a subassembly of an alternative prosthetic heart valve storage system similar to that shown above. These components have similar functions to those described above, and thus the same nomenclature will be used.

The subassembly includes a prosthetic heart valve holder 160, a commissure constriction rod 162, an adapter 164, and a packaging clip 166. As explained above, the valve holder 160 includes outwardly-projecting legs 168 that attach to an inflow end of a prosthetic heart valve 170 with sutures 172, as seen in FIGS. 13A and 13B. The holder 160 includes a central aperture which closely receives the commissure constriction rod 162. As with the above-described embodiment, the rod 162 displaces axially through the holder 160 and eventually contacts and tensions portions 172' of the attachment sutures that extend between valve commissure posts 174 and cross the flow axis.

The adapter 164 also includes a ring-shaped outer body 180 defining a central aperture and three outwardly-projecting legs 182 that cover the valve holder legs 168. The adapter 164 features a bridge extending across its aperture and having a threaded nut 184 centered thereon. The threaded nut 184 projects axially upward from the elevation of the ring-shaped outer body 180, and includes lugs 186 that permit a central collar 188 of the packaging clip 166 to be snapped to the adapter 164, as seen best in FIG. 15A.

The commissure constriction rod 162 defines a plurality of lockout pawls 190 positioned on the ends of flexible fingers formed in the vertical walls of a body portion 192. The body portion 192 has a closed bottom end and an open top surmounted by an outwardly-extending rim 194. The size and shape of the body portion 192 fits closely through the aperture of the holder 160, with the lockout pawls 190 being cammed inward and springing outward upon passage therethrough. The top rim 194 limits downward movement of the rod 162 through the holder 160. The rod 162 further defines vertical channels or slots 196.

Similar to the sequence described above, the combination of the commissure constriction rod 162 and adapter 164, as seen in FIG. 13A, is brought down over the top of the combination of the valve holder 160 and valve 170. Although not shown, the adapter 164 couples to the valve holder 160 with attachment sutures. As before, the legs 182 of the adapter 164 cover the valve holder legs 168, and at the same time the sutures 172 that attach the valve holder to the valve 170. The vertical slots 196 of the rod 162 permit passage of the bridge of the adapter 164. The packaging clip 166 also fits down along the commissure constriction rod 162 until the central collar 188 can be snapped onto the upstanding threaded nut 184 of the adapter 164, as seen in FIG. 13B.

FIGS. 14A and 14B show the assembled components from FIG. 12 prior to deployment of the commissure constriction rod 162, while FIGS. 15A and 15B show the commissure constriction rod deployed. The prosthetic heart valve 170 has been removed for clarity to better show the internal engagement of a threaded delivery shaft 200 with the threaded nut 184 and the commissure constriction rod 162. Specifically, advancing the delivery shaft 200 along the threaded nut 184 eventually causes the distal end of the delivery shaft to contact the closed bottom of the rod 162, forcing the rod downward until the top rim 194 contacts the valve holder 160, as seen in FIG. 15B.

This embodiment also illustrates a feature that permits adaptation of the commissure constriction rod 162 for different sizes of heart valves 170. In particular, the axial distance that the rod 162 travels in order to pull the valve commissure posts 174 inward changes for different sizes of valves; with larger valves requiring a greater axial travel distance. However, the length of the threaded portion of conventional delivery shafts 200 is constant. In order to vary the distance that the rod 162 travels, a small axial post 202 extending upward from the closed bottom end is provided. The axial post 202 includes a concave upper surface that receives and centers the distal end of the delivery shaft 200. By varying the axial height of the post 202, the point at which the delivery shaft 200 engages the commissure constriction rod 162 can be adjusted. For larger valves, the length of the axial post 202 is increased so that the delivery shaft 200 engages the rod 162 earlier, and causes greater travel. Conversely, for smaller valves, the length of the axial post 202 is minimized.

FIGS. 16-18 illustrate key components of another alternative prosthetic heart valve storage system 220 having an integrated worm screw 222. The system 220 includes the worm screw 222, a prosthetic heart valve holder 224, a commissure constriction rod 226 (two parts), a screw couple 228, and an adapter ring 230. The system 220 functions much like the two embodiments described above, though a threaded nut 232 is provided on the valve holder 224 rather than on a separate adapter, and the integrated worm screw 222 replaces part of the function of the threaded end of a delivery handle.

FIGS. 19-20 illustrate the system 220 components from before and after deployment of the commissure constriction rod, and show aspects of the assembly. With reference also to FIG. 17, the valve holder 224 includes a generally ring-shaped body 240 surrounding a central aperture 242 and having a plurality, preferably three, outwardly-projecting valve engagement legs 244. As before, each valve engagement leg 244 includes a downwardly-projecting flange 246 for centering the holder 224 within a sewing ring on the inflow end of a prosthetic heart valve 248. Each leg 244 further includes through holes and cutting guides to permit passage of attachment sutures that extend down the valve commissure posts and across the outflow end between commissure post tips.

The commissure constriction rod 226 includes a generally tubular body 250 extending from a closed bottom end 252 to an open top end 253. The top end 253 couples with a head member 255 having a pair of outwardly extending opposed top flanges 254. The flanges 254 have through holes 256 for receiving sutures to attach to the adapter ring 230, as will be explained. The commissure constriction rod 226 is an assembly of the two components—the tubular body 250 and the head member 255—so that it may be held within the central aperture 242 of the valve holder 224. The head member 255 has downwardly-depending sidewalls 286 that surround the top end 253 of the commissure constriction rod body 250 and split on both sides in two projections 288 that fit within the similarly-sized recesses 290 on each side of the upper end of the rod body. To assemble, the bifurcated rod body 250 inserts up through the central aperture 242 of the valve holder 224 on either side of a bridge 260 on the holder, after which the head member 255 adheres or otherwise fastens to the top end 253, as seen in FIGS. 19A and 19B.

The tubular body 250 of the rod 226 fits closely within the central aperture 242 of the valve holder 224. The body 250 is bifurcated by a pair of vertical slots 258 which permit passage around the bridge 260 on the holder 224. The threaded nut 232 is centered on the bridge 260 and thus passes into the interior of the bifurcated rod 226.

As seen in FIGS. 18A, 19A, and 19B, the commissure constriction rod 226 in an undeployed position fits within the central aperture 242 of the valve holder 224 with the majority of its body 250 above the level of the holder. The worm screw 222 resides within the bifurcated body 250 of the rod 226, and is placed therein by flexing apart the two sides of the body. The bottom end of the worm screw 222 engages the threaded nut 232 on the holder 224, while the top-end includes an outward shelf 262 that abuts the underside of an inwardly-jutting ridge 264 at the top of the rod body 250. The combination of the outward shelf 262 and ridge 264 retain the worm screw 222 in the interior of the bifurcated body 250. The worm screw 222 further includes a keyed head 266 on its proximal end which faces up through the open top end of the rod body 250.

The screw couple 228 comprises a relatively short tubular member having a proximal end 270 with a central opening leading to a lumen, a small circular rib 272 in a midsection thereof, and outward flange 274 towards a distal end, and an open distal end 276 that includes a key (not shown) designed to mate and rotate the keyed head 266 of the worm screw 222. Although a rectangular design of keyed head 266 is shown, other meshing arrangements are possible. As seen in FIG. 19B, the flange 274 of the screw couple 228 fits closely within the upper flanges 254 and rests on the inward ridge 264 of the bifurcated rod body 250. The distal end 276 extends downward such that the key therein engages the keyed head 266 of the worm screw 222.

Still with reference to FIGS. 17 and 19A/19B, the adapter ring 230 comprises a ring-shaped body 280 featuring a pair of opposed flanges 282 having through holes 284. The ring 230 extends down over the screw couple 228 such that the proximal end 270 of the screw couple projects upward, as seen in the assembled views. The screw couple 228 rotates freely within the central aperture of the adapter ring 230. The flanges 282 of the ring 230 align with and rest on the flanges 254 of the commissure constriction rod 226. The alignment of the flanges 254 of the rod 226 and the flanges 282 of the adapter ring 230 ensures alignment of the through holes 256 on the rod flanges 254 and the through holes 284 on the ring flanges 282. The assembled views show these flanges aligned and secured together with attachment sutures 292.

As seen by the sectional assembly in FIG. 19B, rotation of the screw couple 228 causes rotation of the worm screw 222. The screw couple 228 may be rotated by threading the distal end of a conventional valve delivery handle (e.g., handle 150 discussed above) into the opening at the proximal end 270. Although not shown, the inner lumen of the screw couple 228 may have internal threads that mate with threads on a conventional valve delivery handle. Because the worm screw 222 engages the threaded nut 232, clockwise rotation thereof translates the worm screw downward. The bottom end of the worm screw 222 fits within a guide depression 294 on the closed bottom end of the commissure constriction rod 226. As the worm screw 222 moves downward, it pushes the commissure constriction rod 226 relative to the surrounding valve holder 224. Ultimately, the worm screw 222 forces the rod 226 down into the position shown in FIGS. 20A and 20B. Outwardly directed lockout pawls 296 on the rod body 256 flex inward as they pass the inner circumference of the valve holder 224, and then spring outward to prevent upward movement of the rod 226. Downward movement of the rod 226 eventually contacts the crossed attachment sutures between the commissure post tips of the prosthetic heart valve 248, forcing them downward into tension which pulls the commissure post tips inward. The valve delivery handle (not shown) may be left engaged with the screw couple 228 and used to manipulate the heart valve into place at the target annulus.

Subsequently, the attachment sutures 292 between the adapter ring 230 and the commissure constriction rod 226 are severed such that the combination of the adapter sleeve and screw couple 228 may be removed, as indicated schematically in FIGS. 20A and 20B. The small circular rib 272 (FIG. 20A) on the screw couple 228 retains the screw couple on the adapter ring 230 so that the two components may be removed together. This step opens up visibility of the valve holder 224 and attached heart valve so that the surgeon can complete the implantation process.

FIG. 21 illustrates a prosthetic heart valve storage system 300 having the capacity to automatically constrict the heart valve commissures upon opening a storage jar. In particular, system includes structure within the storage jar that actuates a mechanism in a heart valve holder for pulling the valve commissure post tips inward upon detaching a jar lid from a bottom portion. The system 300 comprises a storage jar having a bottom portion 302 and a lid 304 that screws thereon. A perforated, generally tubular packaging sleeve 306 fits closely within the jar bottom portion 302 and defines an inner space therein. A packaging clip 308 removably attaches to the top of the sleeve 306 via a plurality of upstanding fingers 310 on the sleeve that mate with openings 312 on the clip.

The packaging clip 308 is generally disc-shaped and has an enlarged rectangular slot 314 open to one side whose edges engage a pair of opposed ears 320 on a prosthetic heart valve holder 322. The holder 322 may be similarly configured to those shown above, with three outwardly extending legs 324 which may be secured to an inflow sewing ring of a prosthetic heart valve (not shown). As before, the attachment sutures extend along the commissures posts and cross over the commissure post tips, much like the valve shown in FIG. 3.

The valve holder 322 includes a central aperture 326 that receives a commissure constriction rod 328 having an upper flange 330. As seen in the views of FIGS. 21 and 24A/24B, the rod 326 includes an inner actuating screw 332 that is engaged by a worm screw 334 extending downward from a center of the jar lid 304. The rod 326 has a generally tubular body 336 with a vertical rib 338 extending outward therefrom. A pair of cantilevered fingers 340 formed by slits in the tubular body 336 feature lockout pawls 342. The vertical rib 338 engages a vertical channel on the inner lumen of the valve holder 322 to prevent relative rotation between.

FIG. 23 is a perspective view looking up into the jar lid 324 to illustrate the worm screw 334 integrated therein, while FIG. 21 shows the jar closed with the worm screw 334 inserted all the way through the commissure constriction rod 328 and an adapter 350. The adapter includes inner threads to which a delivery handle can be attached for manipulating the holder 322 and attached valve during an implant procedure. As with the adapter 44 from FIG. 1, the adapter 350 can easily be removed along with the delivery handle by severing sutures (not shown) connecting the adapter to the commissure constriction rod 328.

To assemble the system 300, the prosthetic heart valve (not shown) and its holder 322 are snapped into place within the rectangular slot 314 on the packaging clip 308. The packaging clip 308 is then snapped into place over the top of the packaging sleeve 306, as seen in FIG. 25. It should be noted that the packaging sleeve 306 includes a plurality of outward protrusions 352 that provide one-way anti-rotational engagement with the sidewalls of the jar bottom portion 302. FIG. 22 illustrates vertical rails 354 on the inside wall of the jar bottom portion 302. The outward protrusions 352 on the sleeve 306 comprise outer ends of cantilevered fingers 356 that flex inward upon relative rotation in a clockwise direction (CW, looking down) within the bottom portion 302, while preventing relative counter-clockwise (CCW) rotation therein. More detail of the anti-rotation cooperation between the sleeve 306 and the jar is provided in co-pending U.S. Pat. No. 8,839,957, entitled PROSTHETIC HEART VALVE PACKAGING SYSTEM, filed Feb. 14, 2011, whose contents are expressly incorporated by reference herein.

FIG. 26 shows the assembly of FIG. 25 inserted up into the jar lid 304, again without the prosthetic heart valve for clarity. To reach this position, the assembly of FIG. 25 is advanced up the worm screw 334 by rotation. Specifically, the inner actuating screw 332 (FIG. 24B) threadingly engages the worm screw 334. Subsequently, the jar lid 306 can be screwed down over the jar bottom portion 302, which typically contains preservative fluid. (It should be noted here that some new techniques enable dry heart valve storage, and thus a preservative solution is not absolutely required.) Because of the one-way anti-rotation cooperation between the sleeve 306 and the jar bottom portion 302, the bottom portion cams the cantilevered fingers 356 inward during this step. The final assembly of the storage system 300 is seen in FIG. 21, with the commissure constriction rod 328 and adapter 350 in an undeployed, raised position relative to the holder 322.

At the time of unpacking the heart valve for use, a technician unscrews the jar lid 304 from the jar bottom portion 302. The cantilevered fingers 356 and outward protrusions 352 on the packaging sleeve 306 interfere with the vertical rails 354 on the inside wall of the jar bottom portion 302 when the jar lid 304 is unscrewed (rotated CCW), which thus prevents the sleeve 306 from concurrently rotating. As a result, the worm screw 334 contacts and displaces the inner actuating screw 332 as a worm screw and follower. This engagement cams the commissure constriction rod 328 and adapter 350 downward through the valve holder 322, and ultimately constricts the valve commissures inward. As mentioned, the lockout pawls 342 on the cantilevered fingers 340 flex inward and then spring outward under the holder 322 to lock the commissure constriction rod 328 in its deployed configuration. The lid 304 may then be removed, exposing the valve packaged within the jar with the valve commissures already constricted. This configuration ensures that the simple act of unscrewing the jar lid deploys the commissure constriction mechanism, thus eliminating any technical instructions. The heart valve is ready to deliver and implant as soon as the jar is opened.

It should be understood that the automated mechanism for constricting the commissures could be incorporated into any of the embodiments described above. For instance, the jar lid might act on a separate element such as the worm screw 222 shown in the embodiment of FIGS. 16-20. Also, components within the various systems described herein can be interchanged, such as by incorporating an adapter such as shown at 44 in FIG. 1 into the system of FIGS. 16-20. In short, unless mutually exclusive, elements of one system may be transferred to other systems. Furthermore, in each embodiment a threaded member is used to displace the respective commissure constriction rod; e.g., the threaded delivery handle 150, the worm screw 222, and the worm screw 334. Each of these and other like devices can be collectively referred to as "threaded members."

FIG. 27 shows components of a further prosthetic heart valve storage system similar to that shown in FIGS. 21-22, but having an alternative holder clip 360 attached to the top of a packaging sleeve 306. Like parts will be given like part numbers. As before, the clip 360 retains a valve holder 322 suspended over the cavity within the sleeve 306. Specifically, the holder 322 includes a pair of opposed ears 320 that are retained on a further central aperture edge 362 of the clip 360, as seen in FIG. 28.

As detailed in FIG. 28, the alternative holder clip 60 includes two halves 364a, 364b that mesh together generally along a diametric mid-line and combine to form a circular disk. Each clip half 364a, 364b includes a pair of tab extensions 370 and a pair of tab receptacles 372, one of each on either side of the central aperture edge 362. Each tab extension 370 fits closely into a tab receptacle 372 of the other half—with the extensions above the receptacles. The combination is seen in FIG. 27.

Figure 29:
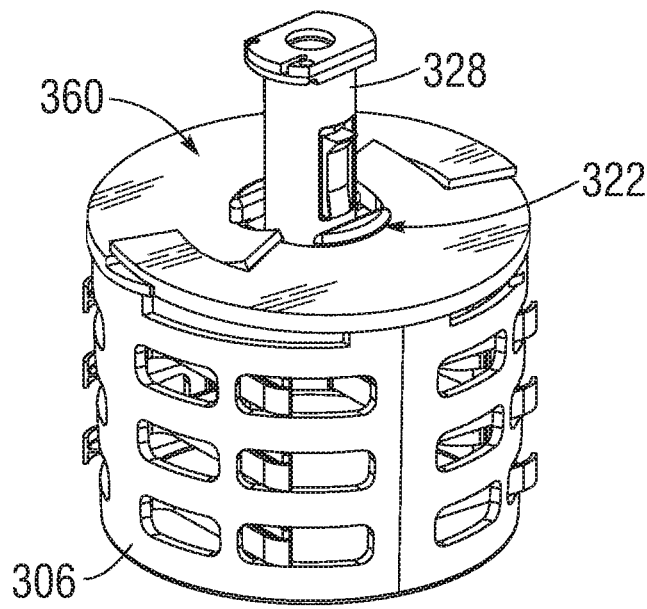
FIG. 29 shows the prosthetic heart valve storage system components of FIG. 27 assembled.

FIG. 29 shows the prosthetic heart valve storage system components of FIG. 27 assembled, with the valve holder 322 retained on the holder clip 360. The holder clip 360 fastens to the top of the packaging sleeve 306 such as via the upstanding fingers 310 on the sleeve within notches or openings in the clip (not shown). The commissure constriction rod 328 is shown in the raised position which occurs by opening the jar lid as described above. The sleeve 306 may be removed from the jar or left on place prior to removal of the valve therefrom.

Figure 30A:
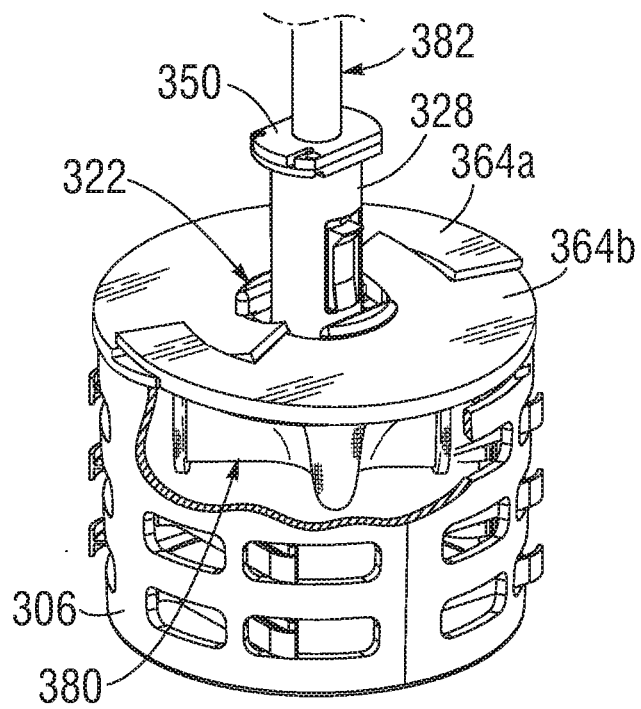
FIGS. 30A and 30B illustrate two steps in a process of removing a prosthetic heart valve from within the packaging sleeve by simply pulling it up past the alternative holder clip.
Figure 30B:
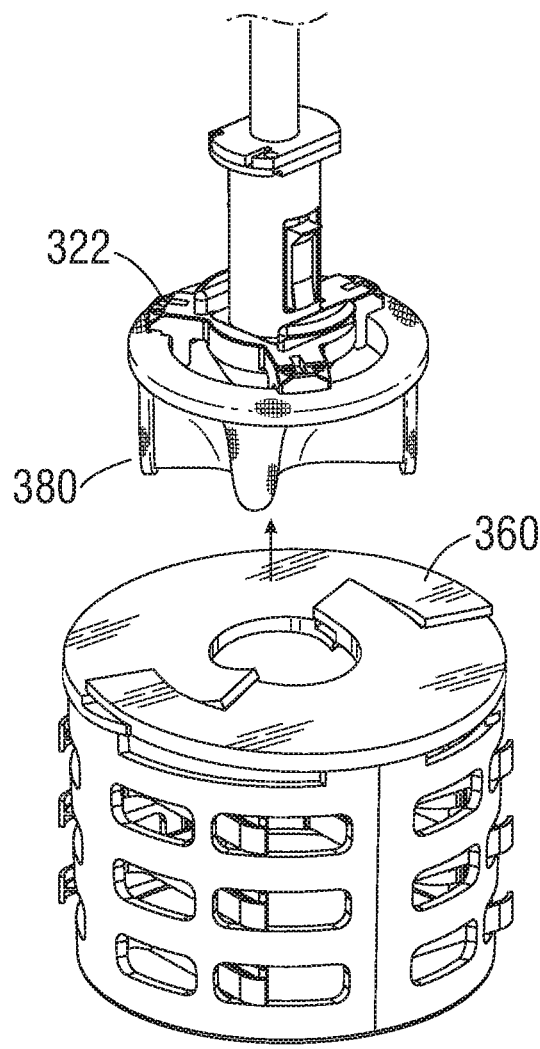

FIGS. 30A and 30B illustrate two steps in a process of removing a prosthetic heart valve 380 from within the packaging sleeve 306 by simply pulling it up past the alternative holder clip 360. First, a delivery handle or rod 382 screws into the throughbore of the adapter 350 coupled to the commissure constriction rod 328. While bracing the sleeve 306 and/or clip 360, the user pulls the rod 382 upward causing the holder 322 and valve 380 to bend the inner edges of the clip halves 364a, 364b upward, and eventually to pull free of the clip 360. The material of the clip 360 is such that the tab extensions 370 are easily flexed upward (unfold) to present minimal resistance to removal of the valve 380. One possible material is a flexible nylon or polyethylene. In this way, the technician need not first remove the clip with the valve from the sleeve, and then pull the clip off of the valve holder—both steps are done at once.

Additionally, the design of the tab extensions 370 and tab receptacles 372 is such that they provide some stiffness to downward pressure. Therefore, the delivery rod 382 can be pushed downward against a reaction force while screwing it into the adapter 350. The clip 360 may also be retrofit to other valve packaging systems, and is not limited to the environment shown.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A storage and handling assembly for a flexible leaflet prosthetic heart valve that helps prevent suture looping, comprising:

a heart valve having a proximal or inflow end and a distal or outflow end and defining a proximal-distal flow axis therebetween, the valve including a plurality of generally axially-extending flexible commissure posts that end in tips circumferentially-spaced around the outflow end that support occluding flexible leaflets of the heart valve;

a valve holder that contacts the inflow end of the heart valve;

a plurality of attachment sutures connecting the heart valve and valve holder each having a first end tied to the valve holder, a middle section that extends from the first end in a distal direction to the commissure post tips and then extends in a proximal direction back to the valve holder, the valve holder defining a plurality of cutting guides over which pass the middle sections of each of the attachment sutures;

a commissure constriction mechanism convertible from an undeployed position to a deployed position which places the attachment sutures in tension and pulls the commissure post tips inward;

an adapter attached to an inflow side of the valve holder that covers locations of the cutting guides on the holder so as to prevent detachment of the valve holder from the heart valve using the cutting guides prior to removal of the adapter from the valve holder, wherein both the adapter and valve holder have through holes for receiving connection sutures fixed to the adapter that couple the adapter and valve holder together such that severing the connection sutures allows removal of the adapter from the valve holder; and a storage jar for receiving the connected heart valve and valve holder.

2. The assembly of claim 1, wherein the valve holder defines a central aperture and the adapter defines a central aperture generally aligned with the valve holder central aperture, wherein the commissure constriction mechanism has a commissure constriction rod with has an elongated body arranged to slide longitudinally through the valve holder central aperture and adapter central aperture, the commissure constriction rod having a proximal rim larger than the central aperture of the valve holder but smaller than the central aperture of the adapter, wherein the commissure constriction rod moves distally from the undeployed position partially projecting proximally from both the valve holder and adapter through the adapter to the deployed position with the proximal rim in contact with the valve holder central aperture and preventing further distal movement.

3. The assembly of claim 2, wherein the adapter central aperture has a bridge thereacross with a threaded nut centered thereon, and the elongated body of the commissure constriction rod has a closed distal end and an open proximal end, and wherein the assembly includes a male threaded member configured to be screwed through the threaded nut of the adapter until it contacts the closed distal end of and forces the commissure constriction rod in a distal direction from the undeployed position to the deployed position.

4. The assembly of claim 2, wherein each attachment suture middle section extends between two commissure post tips across the flow axis of the valve, and there is at least one attachment suture crossing between each two commissure post tips and intersecting with the other attachment sutures, and when moved to the deployed position a distal end of the commissure constriction rod contacts and distally displaces the intersecting attachment sutures which places the attachment sutures in tension and accordingly pulls the commissure post tips inward.

5. The assembly of claim 1, wherein the commissure constriction mechanism has a commissure constriction rod that moves axially through a central aperture in the valve holder between the undeployed and deployed positions and includes a set of opposed lockout pawls on cantilevered fingers that flex inward during passage through the valve holder central aperture and spring outward on a distal side of the valve holder to maintain the commissure constriction rod in the deployed position.

6. The assembly of claim 1, further including a disc-shaped clip that removably couples to the adapter and extends outward from the heart valve so as to fit closely within the storage jar, the disc-shaped clip interacting with the valve holder in a manner which prevents decoupling from the adapter unless the commissure constriction mechanism has converted to the deployed position.

7. The assembly of claim 6, wherein the disc-shaped clip comprises two flexible halves that mesh together along a mid-line in a manner that resists downward movement of the valve holder but permits the valve holder and heart valve to be axially pulled upward free of the disc-shaped clip.

8. The assembly of claim 6, wherein the disc-shaped clip defines a central aperture through which a commissure constriction rod of the commissure constriction mechanism slides, wherein the commissure constriction rod includes axial slots and the disc-shaped clip includes inwardly-directed lugs that extend within the axial slots, wherein the disc-shaped clip can only be decoupled from the adapter after the commissure constriction rod has reached the deployed position and the lugs are no longer within the axial slots.

9. The assembly of claim 6, further including a generally tubular perforated storage sleeve which couples to the disc-shaped clip with cooperating fingers and slots, the storage sleeve being sized to substantially surround without touching the prosthetic heart valve.

10. The assembly of claim 1, further including a disc-shaped clip that removably couples to the adapter and extends outward from the heart valve so as to fit closely within the storage jar, the disc-shaped clip being coupled to the adapter in a manner which requires removal of the disc-shaped clip laterally from the adapter, and having a directional indicator on a proximal face which indicates a lateral direction of removal.

11. A storage and handling assembly for a flexible leaflet prosthetic heart valve that helps prevent suture looping, comprising:

a heart valve having a proximal or inflow end and a distal or outflow end and defining a proximal-distal flow axis therebetween, the valve including a plurality of generally axially-extending flexible commissure posts that end in tips circumferentially-spaced around the outflow end that support occluding flexible leaflets of the heart valve;

a valve holder that contacts the inflow end of the heart valve and defines a central aperture;

a plurality of attachment sutures connecting the heart valve and valve holder each having a first end tied to the valve holder, a middle section that extends from the first end in a distal direction to the commissure post tips and then extends in a proximal direction back to the valve holder, the valve holder defining a plurality of cutting guides over which pass the middle sections of each of the attachment sutures;

a commissure constriction rod movable from an undeployed position to a deployed position which places the attachment sutures in tension and pulls the commissure post tips inward, the commissure constriction rod having an elongated body with a closed distal end and an open proximal end;

an adapter removably attached using connection sutures distinct from the attachment sutures to an inflow side of the valve holder, the adapter and valve holder being coupled together such that severing the connection sutures allows removal of the adapter from the valve holder, and the adapter defining that defines a central aperture generally aligned with the valve holder central aperture, wherein the commissure constriction rod is arranged to slide longitudinally through the valve holder central aperture and adapter central aperture, and wherein the adapter has a threaded nut and covers locations on the valve holder where the attachment sutures cross over the cutting guides so as to prevent detachment of the valve holder from the heart valve using the cutting guides prior to removal of the adapter from the valve holder;

a male threaded member configured to be screwed through the threaded nut of the adapter until it contacts the closed distal end of and forces the commissure constriction rod in a distal direction from the undeployed position to the deployed position; and a storage jar for receiving the connected heart valve and valve holder.

12. The assembly of claim 11, wherein the elongated body of the commissure constriction rod has a proximal rim larger than the central aperture of the valve holder but smaller than the central aperture of the adapter, wherein the commissure constriction rod moves distally from the undeployed position partially projecting proximally from both the valve holder and adapter through the adapter to the deployed position with the proximal rim in contact with the valve holder central aperture preventing further distal movement of the commissure constriction rod.

13. The assembly of claim 12, wherein the adapter central aperture has a bridge thereacross with the threaded nut centered thereon, and the commissure constriction rod has two opposed vertical slots that extend substantially the entire length of the commissure constriction rod, the slots opening at the proximal rim and ending near to the closed distal end, the slots accommodating movement of the commissure constriction rod past the bridge.

14. The assembly of claim 12, wherein the commissure constriction rod includes a set of opposed lockout pawls on cantilevered fingers that flex inward during passage through the valve holder central aperture and spring outward on a distal side of the valve holder to maintain the commissure constriction rod in the deployed position.

15. The assembly of claim 11, wherein the commissure constriction rod includes a set of opposed lockout pawls on cantilevered fingers that flex inward during passage through the valve holder central aperture and spring outward on a distal side of the valve holder to maintain the commissure constriction rod in the deployed position.

16. The assembly of claim 11, wherein each attachment suture middle section extends between two commissure post tips across the flow axis of the valve, and there is at least one attachment suture crossing between each two commissure post tips and intersecting with the other attachment sutures, and when moved to the deployed position a distal end of the commissure constriction rod contacts and distally displaces the intersecting attachment sutures which places the attachment sutures in tension and accordingly pulls the commissure post tips inward.

17. The assembly of claim 11, further including a disc-shaped clip that removably couples to the adapter and extends outward from the heart valve so as to fit closely within the storage jar, the disc-shaped clip interacting with the valve holder in a manner which prevents decoupling from the adapter unless the commissure constriction rod has moved to the deployed position.

18. The assembly of claim 17, wherein the disc-shaped clip defines a central aperture through which the commissure constriction rod slides, wherein the commissure constriction rod includes axial slots and the disc-shaped clip includes inwardly-directed lugs that extend within the axial slots, wherein the disc-shaped clip can only be decoupled from the adapter after the commissure constriction rod has reached the deployed position and the lugs are no longer within the axial slots.

19. The assembly of claim 17, wherein the disc-shaped clip has cantilevered distal latches that engage the adapter and enable easily removal by pulling the disc-shaped clip laterally off of the adapter.

20. The assembly of claim 11, further including a disc-shaped clip that removably couples to the adapter and extends outward from the heart valve so as to fit closely within the storage jar, the disc-shaped clip being coupled to the adapter in a manner which requires removal of the disc-shaped clip laterally from the adapter, and having a directional indicator on a proximal face which indicates a lateral direction of removal.

* * * * *